(12) United States Patent
Nakajima et al.

(10) Patent No.: US 9,888,874 B2
(45) Date of Patent: Feb. 13, 2018

(54) STIMULUS PRESENTATION SYSTEM

(75) Inventors: Akiko Nakajima, Tokyo (JP); Hiroki Sato, Tokyo (JP); Takushige Katsura, Tokyo (JP); Hirokazu Atsumori, Tokyo (JP); Tsukasa Funane, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 438 days.

(21) Appl. No.: 14/407,556

(22) PCT Filed: Jun. 15, 2012

(86) PCT No.: PCT/JP2012/065319
§ 371 (c)(1),
(2), (4) Date: Dec. 12, 2014

(87) PCT Pub. No.: WO2013/186911
PCT Pub. Date: Dec. 19, 2013

(65) Prior Publication Data
US 2015/0141865 A1    May 21, 2015

(51) Int. Cl.
*A61B 5/16* (2006.01)
*A61B 5/00* (2006.01)
*A61M 21/00* (2006.01)

(52) U.S. Cl.
CPC .......... *A61B 5/168* (2013.01); *A61B 5/0075* (2013.01); *A61B 5/162* (2013.01); *A61B 5/6803* (2013.01); *A61M 21/00* (2013.01); *A61M 2021/005* (2013.01); *A61M 2021/0027* (2013.01); *A61M 2205/3306* (2013.01); *A61M 2205/50* (2013.01); *A61M 2230/10* (2013.01); *A61M 2230/62* (2013.01); *A61M 2230/63* (2013.01)

(58) Field of Classification Search
CPC ......... A61B 5/16; A61B 5/0075; A61B 5/161; A61B 5/162; A61B 5/164; A61B 5/165; A61B 5/167; A61B 5/168; A61M 21/00; A61M 2021/004; A61M 2021/005
See application file for complete search history.

(56) References Cited

U.S. PATENT DOCUMENTS

| | | | |
|---|---|---|---|
| 5,311,877 A | 5/1994 | Kishi | |
| 5,676,138 A * | 10/1997 | Zawilinski | A61B 3/113 128/905 |
| 7,774,052 B2 * | 8/2010 | Burton | A61B 5/0476 600/544 |

(Continued)

FOREIGN PATENT DOCUMENTS

| | | |
|---|---|---|
| JP | 05-049626 A | 3/1993 |
| JP | 2980295 B2 | 9/1999 |

(Continued)

OTHER PUBLICATIONS

Psicologia "Reversal Theory: A New Approach to Motivation, Emotion and Personality" 1989.*

*Primary Examiner* — Michael C Stout
(74) *Attorney, Agent, or Firm* — Mattingly & Malur, PC

(57) ABSTRACT

The present invention provides a stimulus presentation system which determines a mental state and changes presentation contents of a problem based on the determined mental state. The system determines the mental state by measuring gaze and cerebral function of a user, and changes presentation contents of a problem based on the determined mental state.

8 Claims, 26 Drawing Sheets

(56) References Cited

U.S. PATENT DOCUMENTS

| | | | |
|---|---|---|---|
| 8,677,281 B2* | 3/2014 | Morris | G06F 3/011 |
| | | | 715/772 |
| 2005/0113650 A1* | 5/2005 | Pacione | A61B 5/411 |
| | | | 600/300 |
| 2007/0202477 A1* | 8/2007 | Nakagawa | A61B 5/14553 |
| | | | 434/236 |
| 2008/0214903 A1* | 9/2008 | Orbach | G06Q 50/22 |
| | | | 600/301 |
| 2010/0211439 A1* | 8/2010 | Marci | H04N 21/84 |
| | | | 705/7.29 |
| 2011/0066082 A1* | 3/2011 | Duffy | A61B 5/1113 |
| | | | 600/595 |
| 2011/0105859 A1* | 5/2011 | Popovic | A61B 5/0205 |
| | | | 600/301 |
| 2011/0295086 A1 | 12/2011 | Nakada et al. | |
| 2012/0083668 A1* | 4/2012 | Pradeep | A61B 5/04015 |
| | | | 600/300 |
| 2012/0125337 A1* | 5/2012 | Asanoi | A61B 5/0816 |
| | | | 128/204.23 |
| 2012/0150449 A1* | 6/2012 | Dobin | A61B 5/04842 |
| | | | 702/19 |
| 2012/0295589 A1* | 11/2012 | Alexander | H04L 63/0861 |
| | | | 455/411 |
| 2014/0336539 A1* | 11/2014 | Torres | A61B 5/11 |
| | | | 600/595 |

FOREIGN PATENT DOCUMENTS

| | | |
|---|---|---|
| JP | 3369201 B2 | 11/2002 |
| JP | 2007-202822 A | 8/2007 |
| JP | 2007-265377 A | 10/2007 |
| JP | 2010-194176 A | 9/2010 |
| JP | 4772935 B2 | 7/2011 |
| JP | 2012-000449 A | 1/2012 |

\* cited by examiner

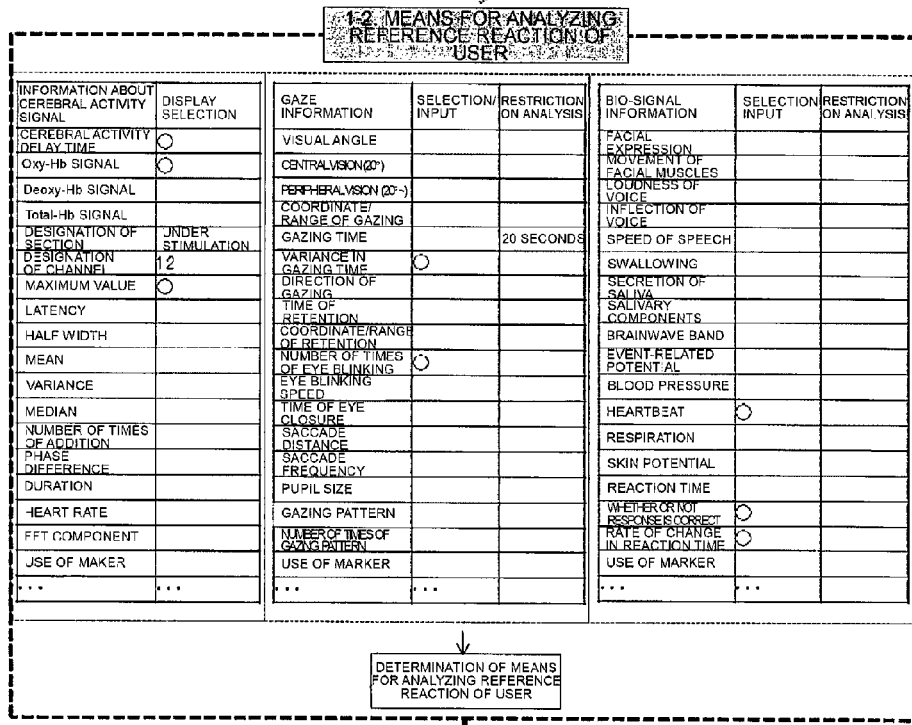
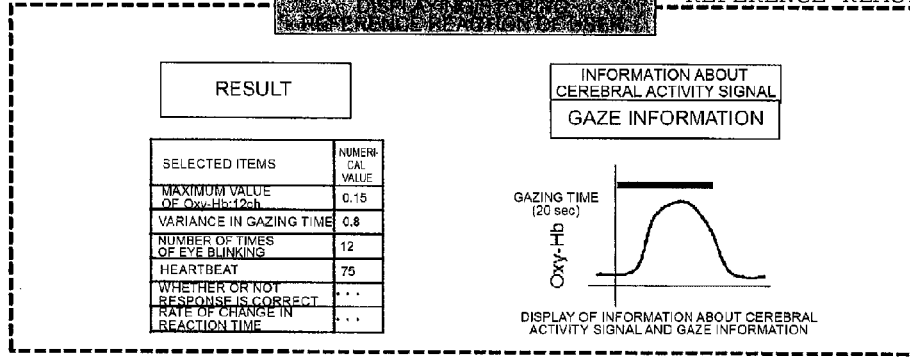
FIG. 5

2-2 MEANS FOR STORING MEASUREMENT
ITEM AND MEASUREMENT SIGNAL

FIG. 9
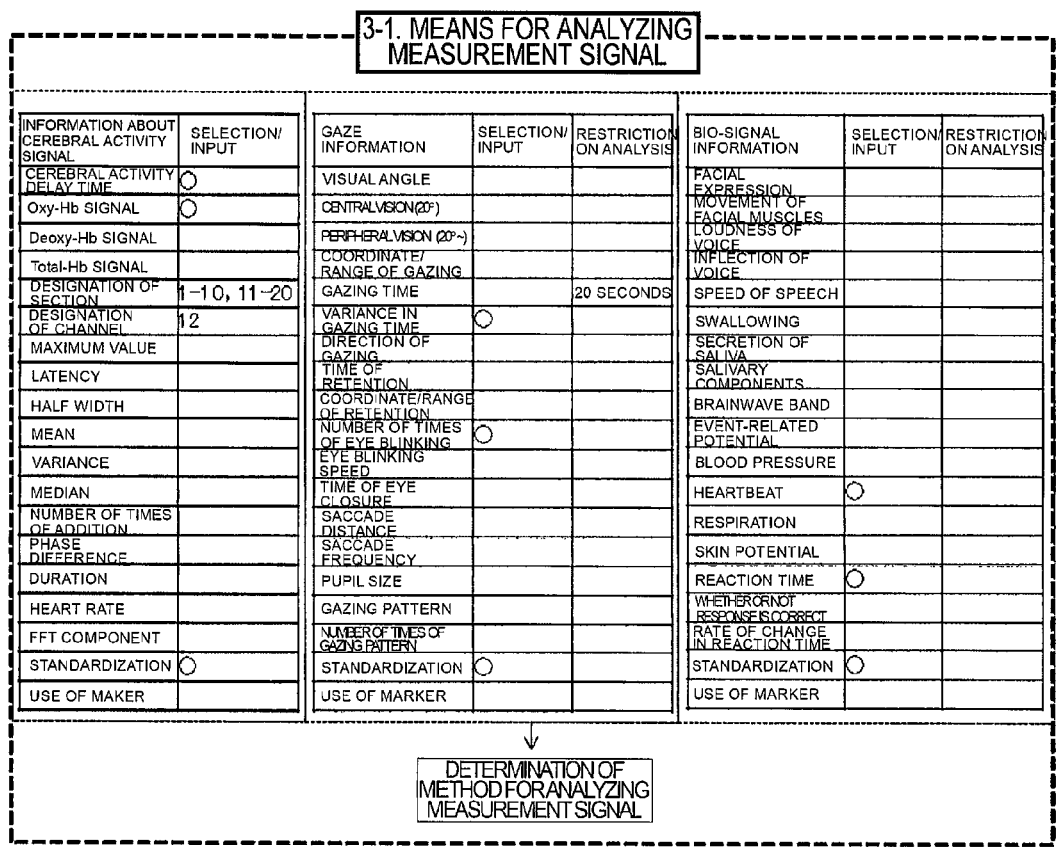
MEANS FOR ANALYZING
MEASUREMENT SIGNALS
AND STORING ANALYSIS
RESULT

FIG. 12

TREND OF (MOTIVATED) MENTAL STATE BASED ON REVERSAL THEORY (Apter,1989)

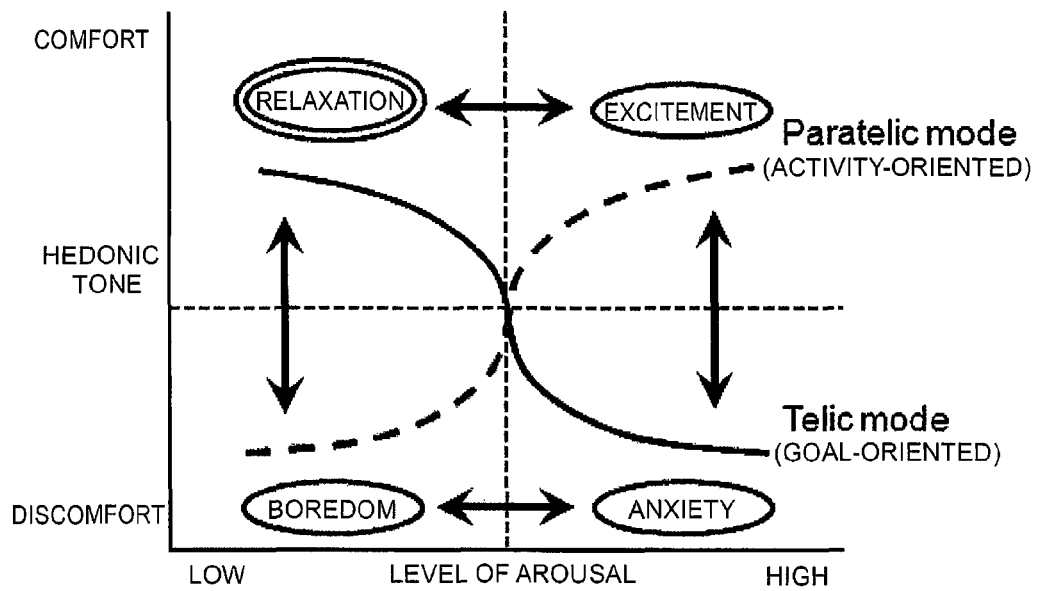

FIG. 13

EXAMPLE OF HOW TO DETERMINE MENTAL STATE

|  | CEREBRAL ACTIVITY OF STIMULUS-RELATED REGION* | CEREBRAL ACTIVITY OF REGIONS OTHER THAN STIMULUS-RELATED REGION | HEART BEAT | EYE BLINKING | VARIANCE IN GAZING TIME |
|---|---|---|---|---|---|
| ANXIETY (telic mode HIGH AROUSAL-DISCOMFORT) | ↑ | ↑ | ↑ | ↑ | ↑ |
| RELAXATION (telic mode LOW AROUSAL-COMFORT) | ↑ | — | ↓ | ↓ | ↓ |
| EXCITEMENT (paratelic mode HIGH AROUSAL-COMFORT) | ↑ | — | ↑ | ↓ | ↓ |
| BOREDOM (paratelic mode LOW AROUSAL-DISCOMFORT) | ↓ | ↓ | ↓ | ↓ | ↓ |

FIG. 17

EXAMPLE OF HOW TO SELECT ITEMS FOR PRESENTATION CONTENT CONVERSION

| CURRENT STATE | CEREBRAL ACTIVITY OF STIMULUS-RELATED REGION | CEREBRAL ACTIVITY OF REGIONS OTHER THAN STIMULUS-RELATED REGION | HEART BEAT | EYE BLINKING | VARIANCE IN GAZING TIME |
|---|---|---|---|---|---|
| ANXIETY (telic mode HIGH AROUSAL-DISCOMFORT) | ↑ | ↑ | ↑ | ↑ | ↑ |

| OPTIMAL STATE | CEREBRAL ACTIVITY OF STIMULUS-RELATED REGION | CEREBRAL ACTIVITY OF REGIONS OTHER THAN STIMULUS-RELATED REGION | HEART BEAT | EYE BLINKING | VARIANCE IN GAZING TIME |
|---|---|---|---|---|---|
| RELAXATION (telic mode LOW AROUSAL-DISCOMFORT) | ↑ | — | ↓ | ↓ | ↓ |

5-3 MEANS FOR CREATING AND STORING TIME TABLES OF MEASUREMENT ITEMS AND PRESERVATION CONTENT CONVERSION

| ITEMS OF PRESENTATION CONTENT | DETERMINED MATTER |
|---|---|
| VISUAL SENSE: COLOR COMBINATION | CHANGE |
| VISUAL SENSE: DISPLAY SPEED | -10% |
| INFORMATION FEEDBACK | PRESENT |
| SUPPORTING COMMENT | PRESENT |

FIG. 18

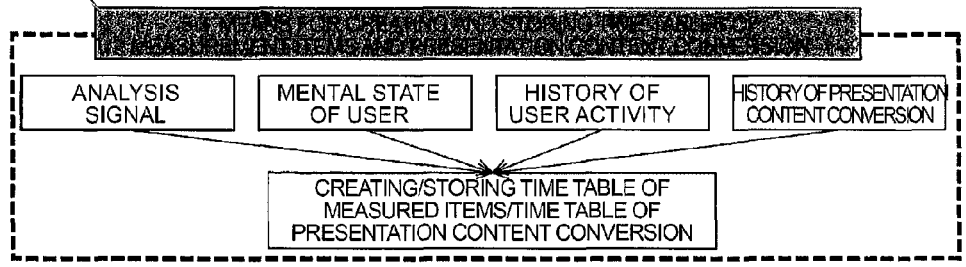

ANALYSIS SIGNAL | MENTAL STATE OF USER | HISTORY OF USER ACTIVITY | HISTORY OF PRESENTATION CONTENT CONVERSION

CREATING/STORING TIME TABLE OF MEASURED ITEMS/TIME TABLE OF PRESENTATION CONTENT CONVERSION 6-1 MEANS FOR DISPLAYING ANALYSIS SIGNAL
6-2 MEANS FOR DISPLAYING MENTAL STATE
6-3 USER ACTIVITY RELATED DISPLAY MEANS

STIMULUS PRESENTATION SYSTEM

TECHNICAL FIELD

The present invention relates to a system that displays information for a user by using gaze information and cerebral function information about the user.

BACKGROUND ART

A technique of estimating the mental state of a user, such as a degree of attention or a degree of concentration, by using information about a gaze or cerebral function of the user and operating an external instrument such as an automobile or a wheelchair has been suggested.

For example, PTL 1 discloses a driver state determining device that can more specifically determine the state of a driver by classifying the state of a driver by three factors including a degree of arousal, a degree of attention and concentration, and a driving ability; detecting at least two pieces of driver information reflecting the respective factors; and determining the state of the driver based on a combination of the detected driver information.

Furthermore, PTL 2 discloses a technique of measuring the distribution of a user's α-wave intensity (cerebral activity fluctuation amount) in the cephalic region and measuring a gaze, and measuring an attention area in the visual field of the user based on the distribution of α-wave intensity and the gaze. PTL 2 also discloses a technique of measuring a pattern of change in the user's α-wave intensity, measuring a degree of attention of the user based on the pattern of change in the α-wave intensity, and controlling the operation of an electric wheelchair according to the measured attention area in the visual field of the user and the measured degree of attention.

CITATION LIST

Patent Literature

[PTL 1] JP-A-2007-265377
[PTL 2] JP-A-2007-202882

SUMMARY OF INVENTION

Technical Problem

The degree of attention or the degree of concentration estimated by the aforementioned techniques in the related art includes a plurality of mental states that causes the degree of attention or the degree of concentration. For example, even when it is estimated that a user is paying attention to or is concentrating on something, whether this is because the user is interested in it or because the user senses danger cannot be estimated. In this way, when a plurality of mental states is present as potential causes, and an external instrument is automatically operated without discriminating between the mental states, there is a possibility that the instrument may not necessarily operate in an appropriate manner.

Therefore, the present invention aims to provide a stimulus presentation system which determines the mental state of a user by measuring the user's gaze and cerebral function and changes presentation contents of a problem based on the determined mental state.

Solution to Problem

An example of a stimulus presentation system of the present invention includes a user setting portion that measures the reference state of a user; a user measurement portion that obtains gaze information and cerebral function information about the user; a signal analysis portion that analyzes signals by correcting a time lag between the gaze information and the cerebral function information; a user determination portion that determines a mental state based on the analyzed signals; a presentation content conversion portion that changes presentation contents of a problem based on the determined mental state; a display control portion that displays the analyzed signal and the determined mental state; and a storage portion that stores the presentation contents converted by means for converting presentation contents, a predetermined measurement item for determining the mental state, and user information.

Advantageous Effects of Invention

According to the present invention, it is possible to determine the mental state of a user by measuring a gaze and cerebral function of the user and to change the presentation contents of a problem based on the determined mental state. That is, it is possible to present a problem more appropriate for the state of a user.

BRIEF DESCRIPTION OF DRAWINGS

FIG. 5 is a view showing an example of how to set a user interface in the user setting portion of the present example, and showing an example of an analysis result.

FIG. 9 is a view showing an example of how to set a user interface in the signal analysis portion of the present example.

FIG. 12 is a view showing mental states based on Reversal Theory.

FIG. 13 is a view showing an example of how to determine a mental state in the present example.

FIG. 17 is a view showing an example of how to select items for presentation content conversion in the present example.

FIG. 18 is a view showing a flowchart relating to measurement items and presentation content conversion of the present example.

DESCRIPTION OF EMBODIMENTS

Example 1

An example of the constitution of the stimulus presentation system according to the present invention will be described based on exemplary embodiments. In the following example, gaze information is obtained by a device using infrared rays, and cerebral function information is obtained by a device that measures a change in cerebral blood volume by using near infrared spectroscopy. However, the gaze information may be obtained by optical bioinstrumentation, potential measurement, image measurement, and the like, and the cerebral function information may be obtained by optical bioinstrumentation, potential measurement, magnetic field measurement, metabolism measurement, and the like.

Figure 1:
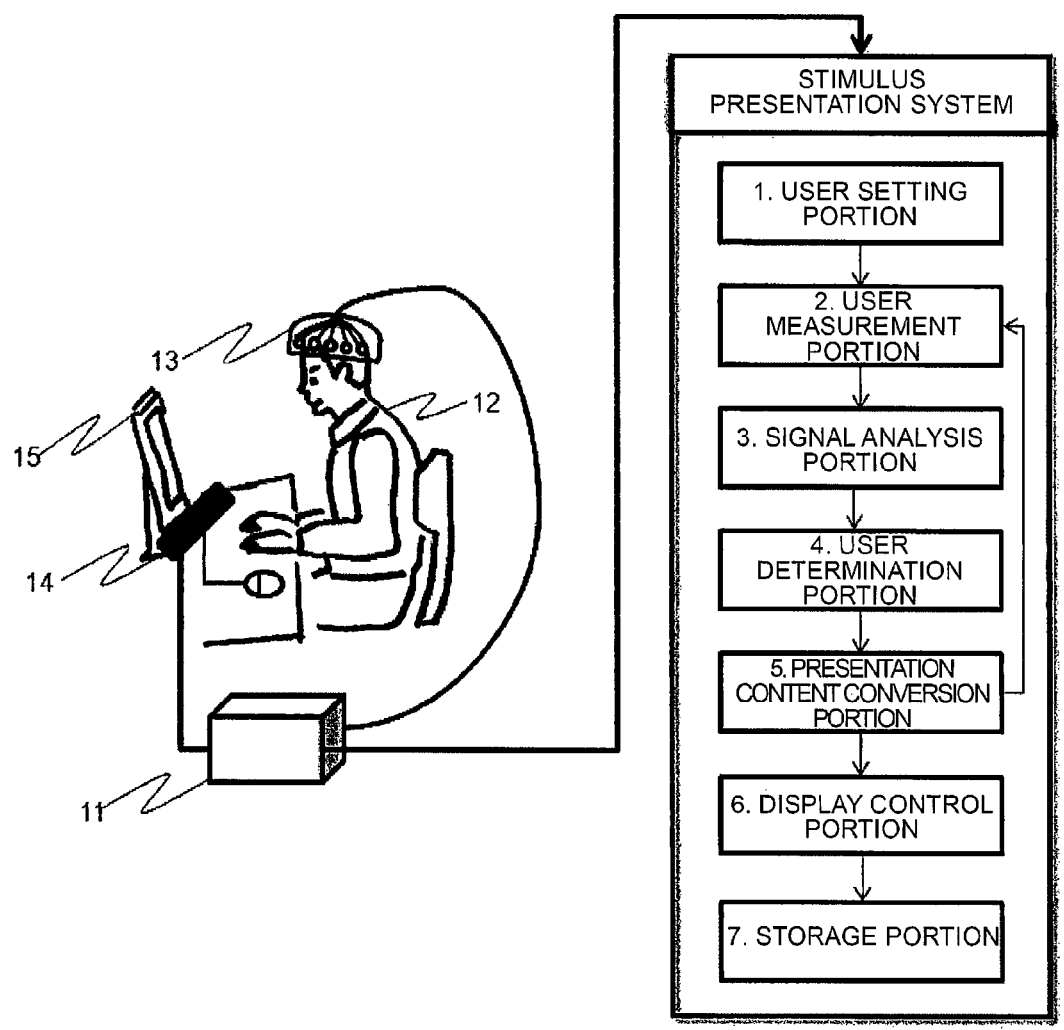
FIG. 1 is a view showing an example of the entire stimulus presentation system of the present invention.

FIG. 1 is a block diagram showing the entire stimulus presentation system of the present example. The stimulus presentation system includes an arithmetic device 11; a cerebral activity information-measuring instrument 13 that has a measurement portion being able to be mounted on the cephalic region of a user 12; a gaze information-measuring instrument 14 that measures the gaze of a user; and a monitor 15 (stimulus presentation portion 15) that presents a stimulus including a problem to a user.

The arithmetic device 11 includes a user setting portion 1 that can set user information and the like via input means; a user measurement portion 2 that can collect information measured by the cerebral activity information-measuring instrument 13, the gaze information-measuring instrument 14, or the like; a signal analysis portion 3 that performs analysis based on the measurement results obtained by the user measurement portion; a user determination portion 4; a presentation content conversion portion 5; a display control portion 6; and a storage portion 7. Herein, the storage portion 7 is not necessarily installed in the arithmetic device, and may be connected to the arithmetic device through external connection means by wired communication means or wireless communication means.

The stimulus presentation system also includes input means for providing and inputting information necessary for making a response to a presented problem, user settings, initial setting of a problem, and the like. Specifically, the system includes a keyboard, a mouse, or the like, but the input means is not limited to the keyboard or the mouse. For example, the input means can be constituted with a touch panel that makes it possible to input information by directly touching the monitor 15.

Figure 24:
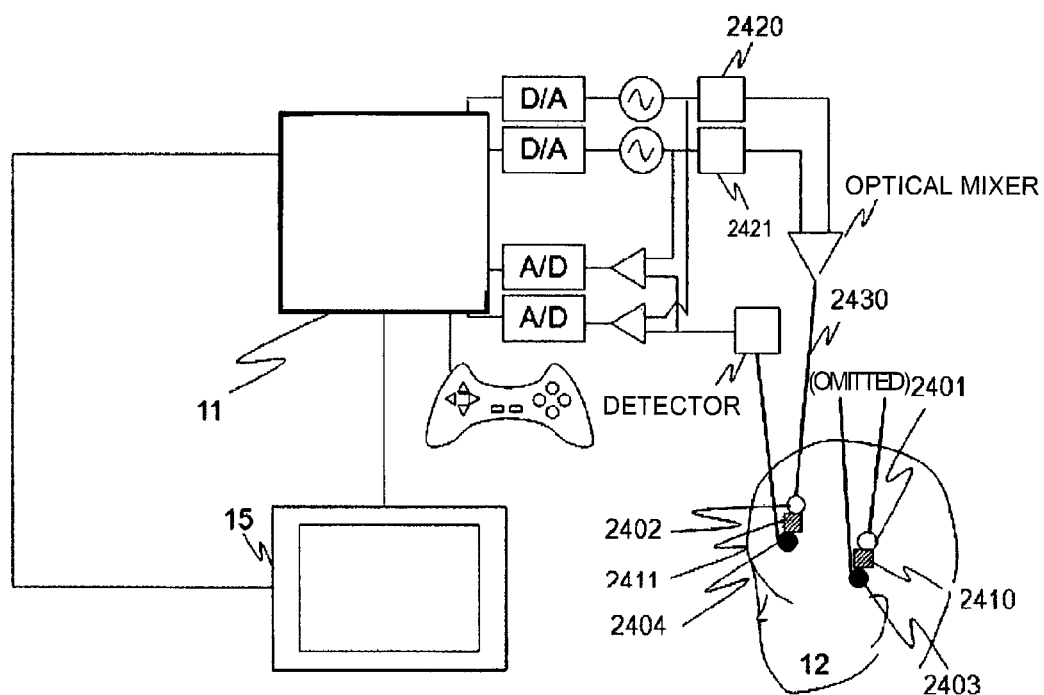
FIG. 24 is a view showing an example of a cerebral function information-measuring instrument.

Herein, a specific example of the cerebral activity information-measuring instrument 13 will be described by using FIG. 24. FIG. 24 is a schematic constitutional view of the cerebral activity information-measuring instrument 13.

In the present example, the cerebral activity information-measuring instrument 13 has light irradiation means 2401 and 2402 which irradiate a subject with light and each of which is present singly or present in plural numbers; and light detection means 2403 and 2404 which detect light transmitted through or reflected from a subject and each of which is present singly or present in plural numbers.

Furthermore, the light irradiation means and the light detection means have a plurality of measurement points in the form of a combination of the plurality of measurement points (hereinafter, also referred to as "ch"; a first measurement point 2410 and a second measurement point 2411). The respective measurement points are mounted on a subject in spatially different positions. Herein, the light irradiation means irradiates a subject with light of two wavelengths from wavelengths of about 600 nm to 900 nm that can be transmitted through a biological body. Specifically, a laser diode or an LED is used as a light source 2420 or 2421; the light is brought into direct contact with a subject 12, or alternatively, by using an optical fiber 2430, light guided from the light sources 2420 and 2421 is brought into contact with the subject 12, whereby the subject 12 is irradiated with the light. As the detection means, a silicon photodiode, an avalanche photodiode, a photomultiplier, or the like is used. Similarly to the light irradiation means, the light detection means directly detects the light on the subject 12, or alternatively, the light detection means detects light by bringing the optical fiber 2430 into contact with the subject 12 and guiding light by using the optical fiber 2430.

Moreover, the cerebral activity information-measuring instrument 13 is connected to the monitor 15 that presents one kind or plural kinds of problems to the subject 12. The cerebral activity signals at each of the measurement points 2410 and 2411 of the subject 12 are detected one by one by the detection means. In the user measurement portion 2 installed in the arithmetic device 11, the detected results are used to obtain the cerebral activity signal at the measurement points of the user 12 with respect to the presented problem.

Figure 25A:
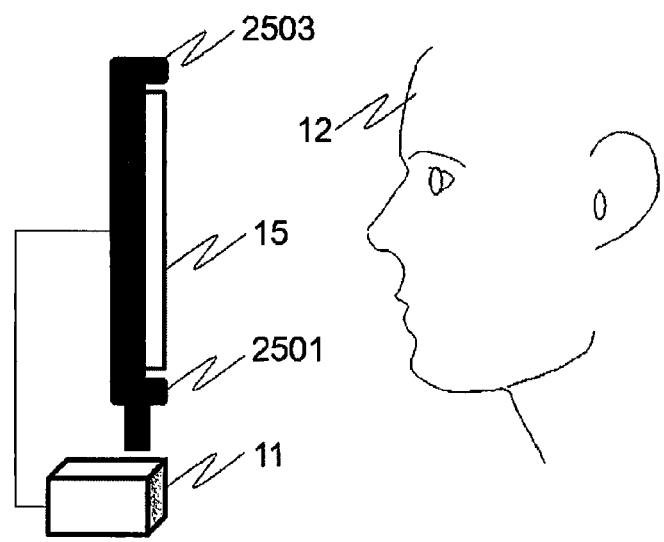
FIGS. 25A, 25B and 25C are views showing examples of a gaze information-measuring instrument.
Figure 25B:
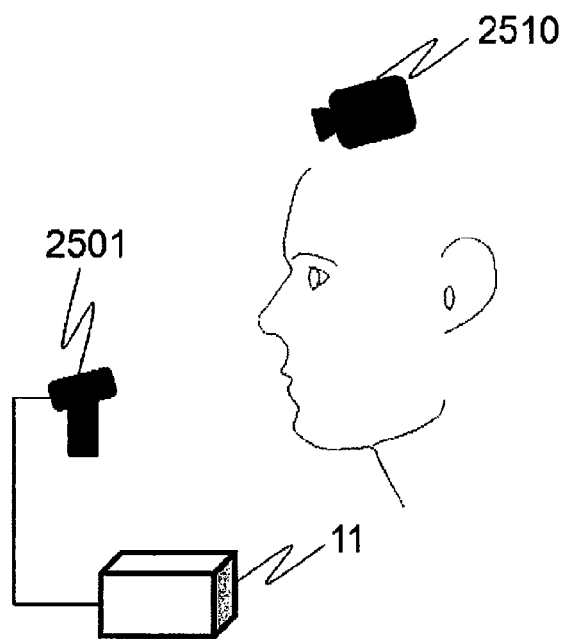
Figure 25C:
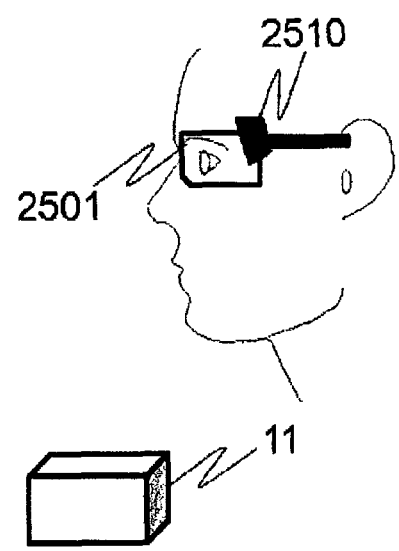

Next, by using FIG. 25, a specific example of the gaze information-measuring instrument 14 will be described below. FIG. 25 is a schematic constitutional view of the gaze information-measuring instrument 14. As shown in FIG. 25A, the gaze information-measuring instrument 14 in the present example has a gaze measuring portion 2501 which includes the irradiation means irradiating the cephalic region of the subject 12 with light and the light detection means detecting the light reflected from the eyeballs of the subject 12; and cephalic position detection means 2502 which detects the cephalic position of the subject 12 by image analysis. The monitor 15 that presents a stimulus such as an image or voice is connected to the subject 12. Specifically, by using infrared light, the gaze information-measuring instrument 14 measures the subject in a non-contact manner. From the signals obtained by the detection means, gaze information is calculated in the arithmetic device 11. In the gaze information-measuring instrument 14 shown in FIG. 25B, the gaze information about the subject 12 can be measured without using the monitor 15. If an image recording instrument 2510 is put on the cephalic region or on the back of the subject 12, the images before the eyes of the subject 12 are recorded, and the signals obtained by the gaze measuring portion 2501 are calculated as gaze information in the arithmetic device 11. The gaze information-measuring instrument 14 shown in FIG. 25C is an example of the gaze measuring portion 2501 that can be wearable as eyeglasses and has the light irradiation means and the light detection means. The images before the eyes of the subject 12 are recorded by the image recording instrument 2510, and in the arithmetic device 11, the gaze information is calculated. The arithmetic device 11 and the gaze information-measuring instrument 14 shown in FIGS. 25A to 25C can perform communication such as wired communication or wireless communication.

Figure 2:
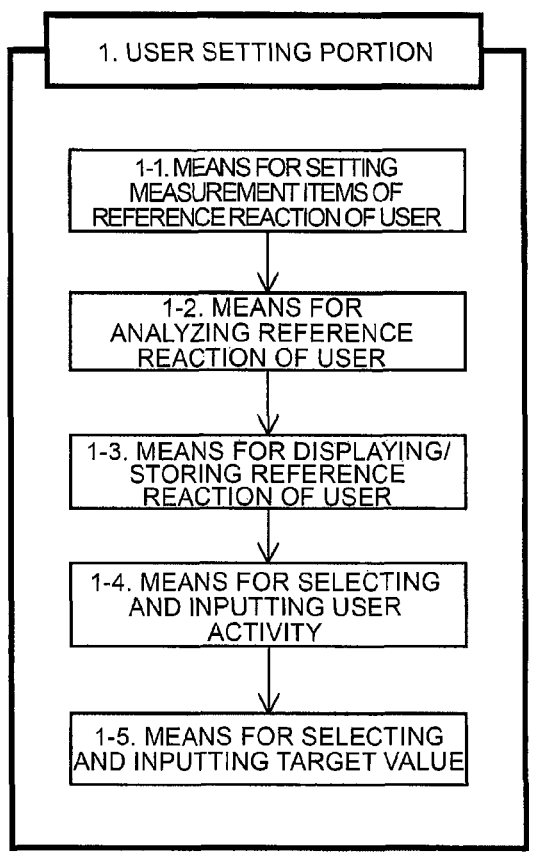
FIG. 2 is a view showing a flowchart of a user setting portion of the present example.

In the present example, the user setting portion 1 in the arithmetic device 11 is constituted with subordinate means 1-1 to 1-5 shown in FIG. 2. Herein, the basic state of a user, who has not yet solved a problem, is measured and analyzed, and types or target values of user activity are set. By comparing the basic state of the user, who has not yet performed an activity, with the state of the user who is performing an activity, the state of a user who is performing the activity can be more appropriately determined.

Figure 3:
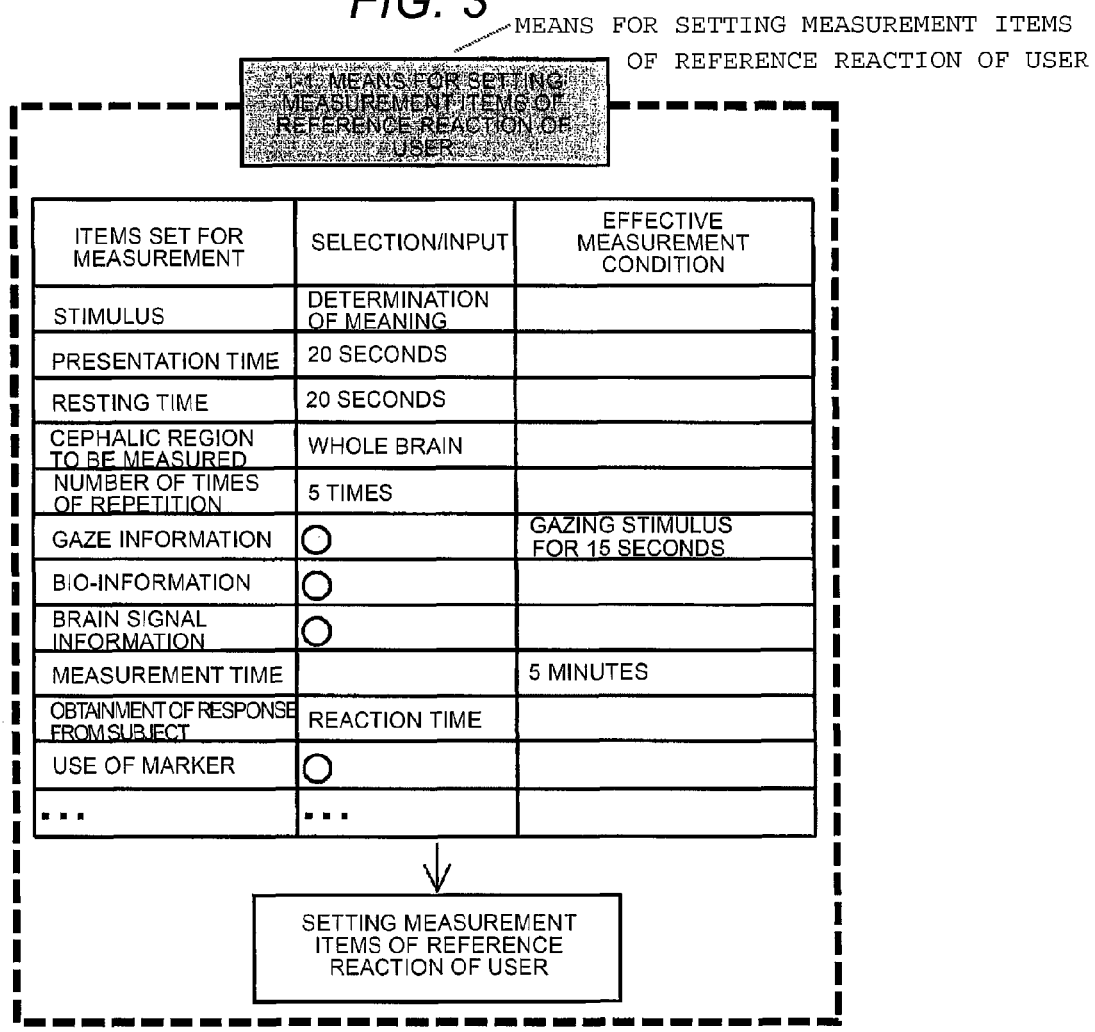
FIG. 3 is a view showing an example of how to set a user interface in the user setting portion of the present example.

In means for setting measurement item of reference reaction of user 1-1, as shown in FIG. 3, from among "stimulus", "presentation time", "resting time", "region to be measured", "number of times of repetition", "gaze information", "bio-information", "signal information", "measurement time", "obtainment of response from subject", and "use of marker", any one item can be selected or input as a measurement item to be set. Other items may be newly added to the measurement item to be set, and the aforementioned items can be used as effective measurement conditions. The effective measurement conditions refer to conditions for selecting the measured signals. According to the procedure described so far, setting of measurement items of reference reaction of a user is completed.

In FIG. 3, "determination of meaning" is set for the "stimulus"; "20 seconds" is set for the "presentation time"; "20 seconds" is set for the "resting time"; "whole brain" is set for the "region to be measured"; "5" is set for the "number of times of repetition"; "performed" is set for the "measurement of gaze information"; "performed" is set for the "measurement of bio-information"; "reaction time" is set for the "obtainment of response from subject"; "yes" is set for the "use of marker"; and as the effective measurement conditions, "15 seconds" is set for the "gazing stimulus", and "5 minutes" is set for the "measurement time".

Figure 4:
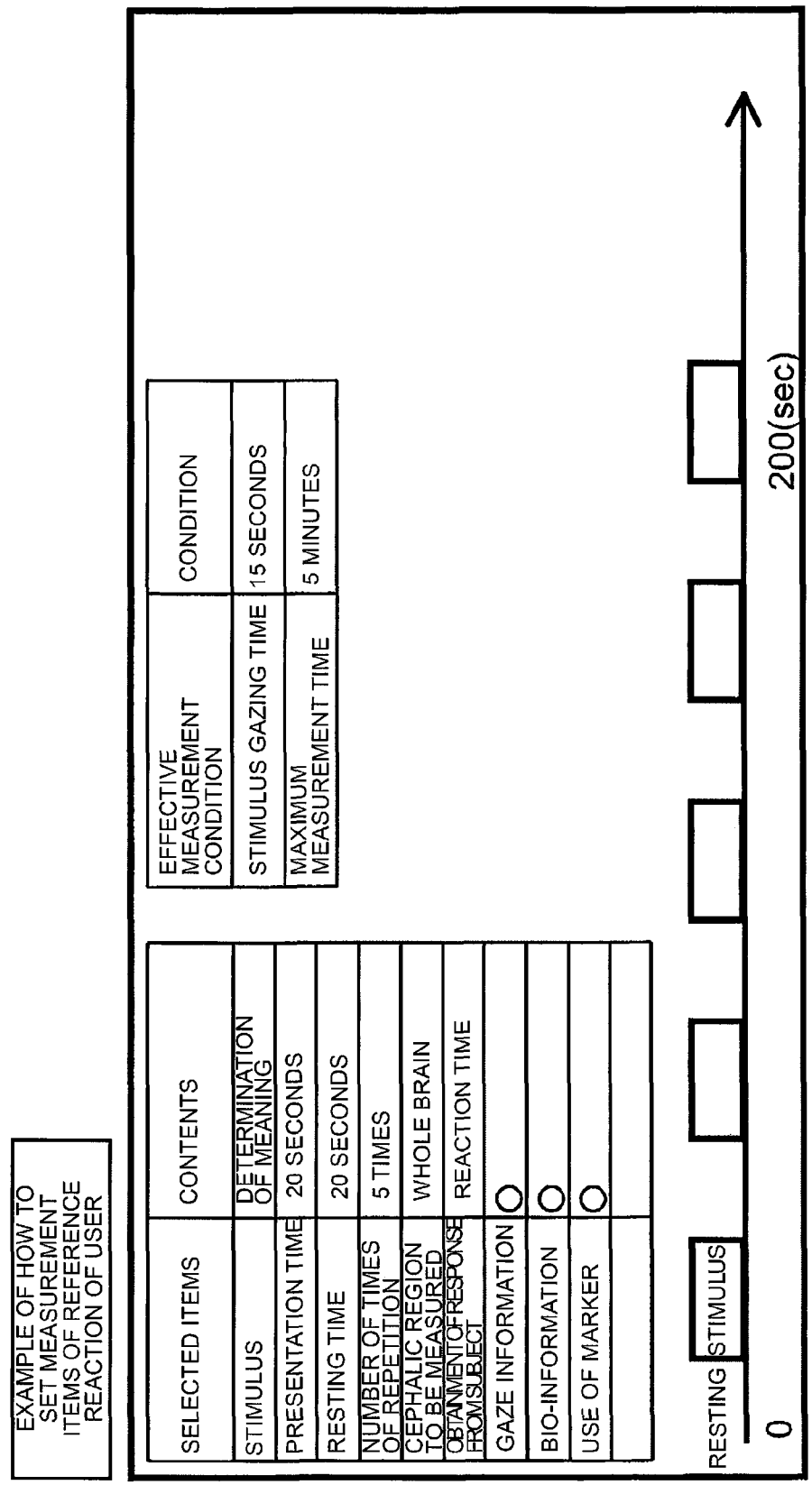
FIG. 4 is a view showing an example of how to set measurement items in the user setting portion of the present example.

In this case, the contents shown in FIG. 4 are set as the measurement items of reference reaction of a user, and as shown in the lower portion of FIG. 4, the resting time and the stimulus time are repeated in a time-series manner. The "use of marker" shows that a time marker is placed at the starting point of the stimulus and at the ending point of the stimulus. Furthermore, under the effective measurement conditions, when the gazing time is equal to or longer than 15 seconds within the time given to solve the problem, the cerebral activity signal is obtained, and when the gazing time is equal to or shorter than 15 seconds, the cerebral activity signal is not obtained. At a point in time when such effective data has been obtained 5 times, the measurement ends. However, because the maximum measurement time is set to be 5 minutes, the measurement is performed for up to 5 minutes. The stimulus is presented on a monitor or presented through a speaker, but writing means such as paper or a pen may also be used. When "use of marker" is set as an effective measurement condition, the time marker is used at a point in time when the effective measurement condition is satisfied.

Because the cerebral activity signal is measured as a reaction with respect to a problem, there is a premise that a user perceives and handles the problem. However, even when the problem is presented to the user, whether the user actually perceives and handles the problem is unclear. The gazing time relates to a fact showing that the user perceives the problem. Consequentially, if the gazing time is set as an effective measurement condition, a cerebral activity signal making it possible to determine that the user has perceived the given problem is obtained, and such a signal becomes more useful data compared to a cerebral activity signal obtained without using the gazing time.

Next, in means for analyzing reference reaction of user 1-2, as shown in FIG. 5, items for analyzing information about cerebral activity signals, gaze information, and bio-signal information can be selected or input.

For the information about cerebral activity signal, from among "cerebral activity delay time", "Oxy-Hb signal", "Deoxy-Hb signal", "Total-Hb signal", "designation of section", "designation of channel", "maximum value", "latency", "half width", "mean", "variance", "median", "number of times of addition", "phase difference", "heart rate", "FFT component", and "use of marker", any one item can be selected or input. Moreover, other items can be newly added to the information about cerebral activity signal.

For the gaze information, from among the "visual angle", "central vision (within 20°)", "peripheral vision (outside of 20°)", "coordinates/range of gazing", "gazing time", "variance in gazing time", "direction of gazing", "time of eyeball retention", "retention/range of eyeball", "number of times of eye blinking", "eye blinking speed", "time of eye closure", "saccade distance", "saccade frequency", "pupil size", "gazing pattern", "number of times of gazing pattern", and "use of marker", any one item can be selected or input. Other items can be newly added to the gaze information.

For the bio-signal information, from among "facial expression", "movement of facial muscles", "loudness of voice", "inflection of voice", "speed of speech", "swallowing", "secretion of saliva", "salivary components", "brainwave band", "event-related potential", "blood pressure", "heartbeat", "skin potential", "reaction time", "whether or not response is correct", "rate of change in reaction time", and "use of marker", any one item can be selected or input. Other items can be newly added to the bio-signal information.

The gaze information and the bio-signal information can also be used as restrictive conditions for analysis that are for assisting the analysis of the information about cerebral activity signals. For example, the gazing time relates to a fact showing that a user has perceived a problem. Consequentially, if the cerebral activity signal making it possible to determine that a user has perceived the problem is used, the information can be more accurately analyzed compared to a case of using the cerebral activity signal obtained without using the gazing time. The information about cerebral activity signals includes various biological effects. Therefore, if the restrictive conditions of analysis are additionally set by using the gaze information or the bio-signal information, accuracy of signal analysis can be further improved.

The reaction, which provides the cerebral activity information, to a stimulus occurs about 5 to 8 seconds after onset of the stimulus. In contrast, the reaction, which provides the gaze information, to a stimulus occurs within 1 second after onset of the stimulus. Accordingly, in order to compare the cerebral activity information with the gaze information relative to the stimulus, the time lag has to be corrected.

Therefore, in analyzing the information about cerebral activity signals, "cerebral activity signal delay time" is selected beforehand. In this way, the time lag between the change in the gaze information and the change in the cerebral activity information relative to the stimulus is corrected, and this makes it possible to analyze the gaze information and the cerebral activity information by comparison. When such an item is selected, "6 seconds" is applied as a delay time, but it is also possible to correct the delay time by inputting any numerical value. Furthermore, the delay time can be applied with reference to a value (mean, median, or the like) calculated from a plurality of existing data.

In means for analyzing reference reaction of user 1-2 of FIG. 5, for the information about cerebral activity signals, "Oxy-Hb signal (oxygenated hemoglobin signal)" is selected. Moreover, "under stimulus" is selected for "designation of section"; "12" is selected for "designation of channel"; and "maximum value" is selected. For the gaze information, "variance in gazing time" and "number of times of eye blinking" are selected. For the bio-signal information, "heartbeat", "whether or not response is correct", and "rate of change in reaction time" are selected. According to the procedure described so far, the means for analyzing reference reaction of user is selected.

Means for displaying/storing reference reaction of user 1-3 displays/stores the results that are obtained by analysis according to the items set by the means for analyzing reference reaction of user 1-2. Herein, the numerical value or the waveform of cerebral activity corresponding to the items selected as shown in the lower portion of FIG. 5 is displayed/stored.

Figure 6:
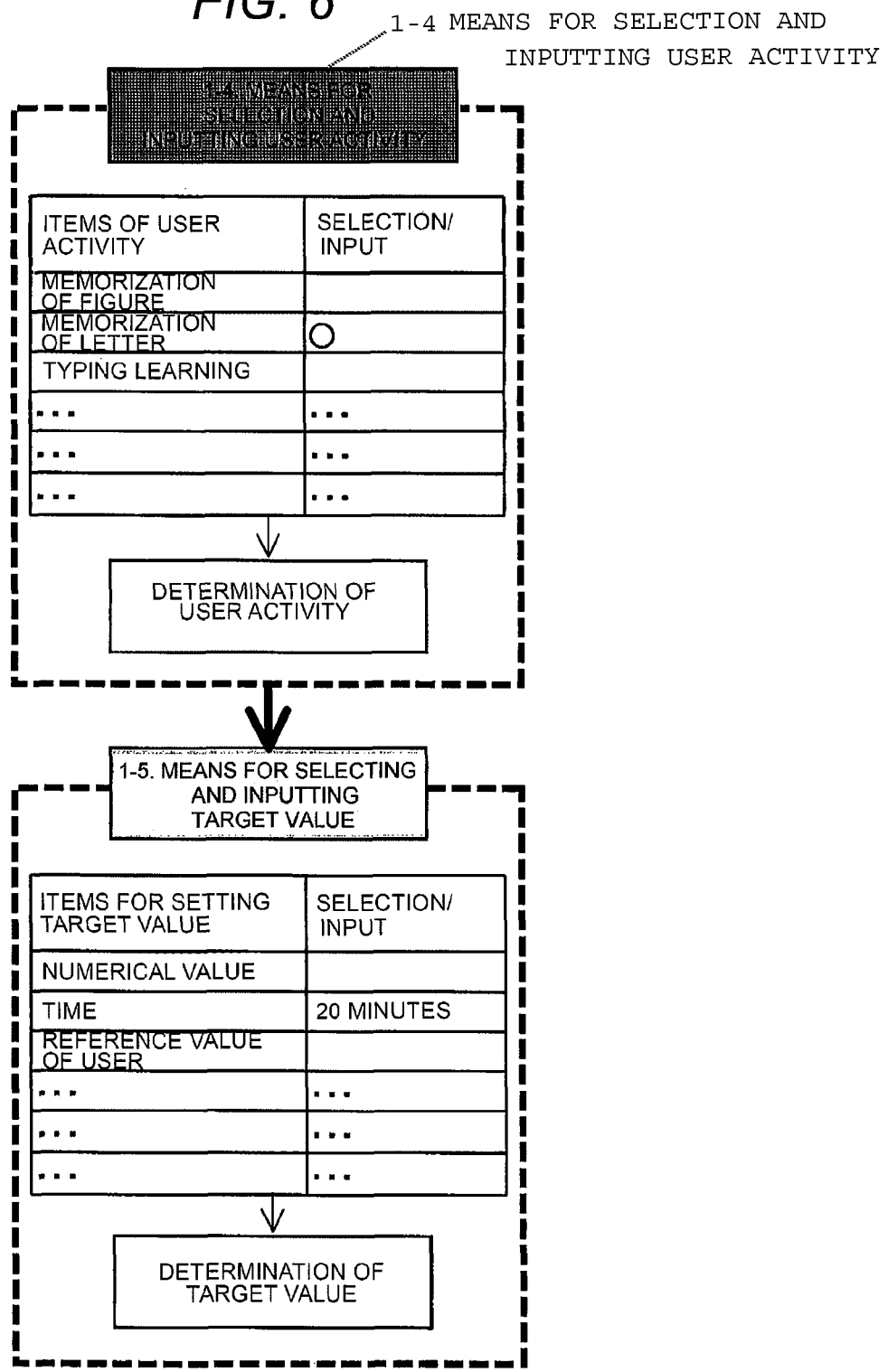
FIG. 6 is a view showing an example of how to set a user interface in the user setting portion of the present example.

In means for selecting and inputting user activity 1-4, as shown in FIG. 6-1, from among "memorization of figure", "memorization of letter", "typing learning", and the like, any one item is selected or input as an item of user activity. Other items can be newly added to the item of user activity. According to the procedure described so far, the user activity is selected. Herein, "memorization of letter" is selected as the activity.

In means for selecting and inputting target value 1-5, as shown in FIG. 6-2, from among "numerical value", "time", "reference value of user", and the like, any one item can be selected or input as an item for setting a target value. Other items can be newly added to the item for setting a target value. According to the procedure described so far, a target value is selected. Herein, "20 minutes" is set for the "time".

Figure 7:
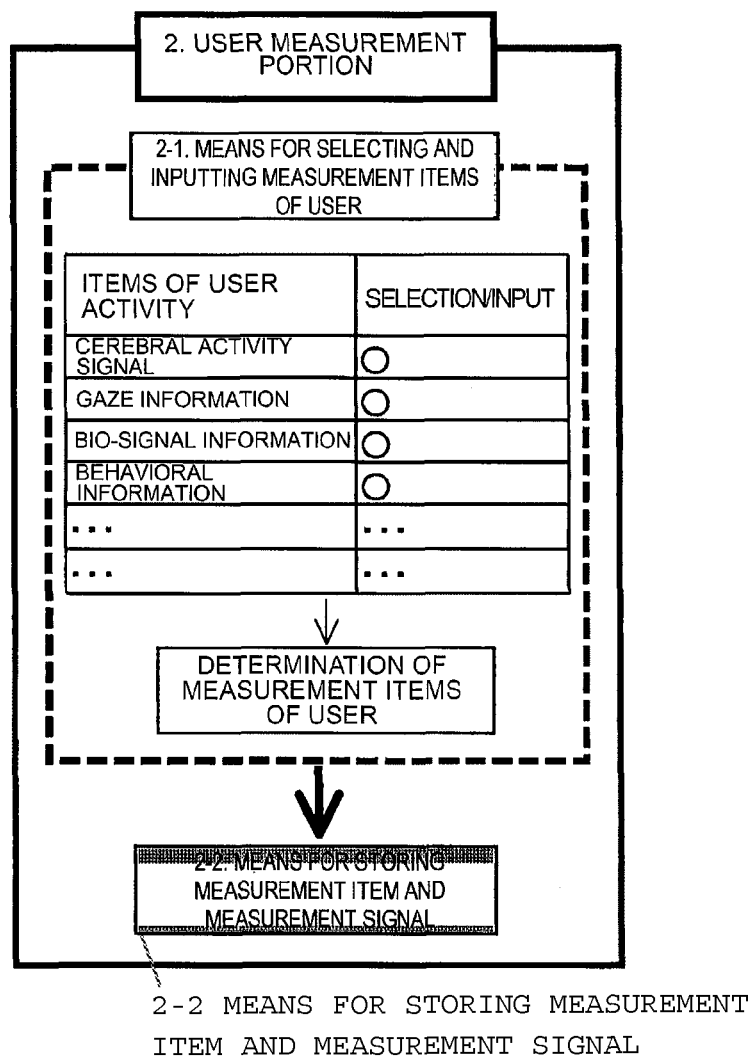
FIG. 7 is a view showing an example of how to set a user interface in the user setting portion of the present example.

The user measurement portion 2 in the stimulus presentation system includes subordinate means 2-1 and 2-2 shown in FIG. 7. In means for selecting and inputting items for measuring user 2-1, from among "cerebral activity signal", "gaze information", "bio-signal information", "behavioral information", and the like, any one item can be selected or input as a measurement item of a user in regard to the user activity. Other items can be newly added to the item for measuring a user. According to the procedure described so far, the measurement item of a user is selected and stored in means for storing measurement item and measurement signal 2-2. Herein, "cerebral activity signal", "gaze information", "bio-signal information", and "behavioral information" are selected.

Figure 8:
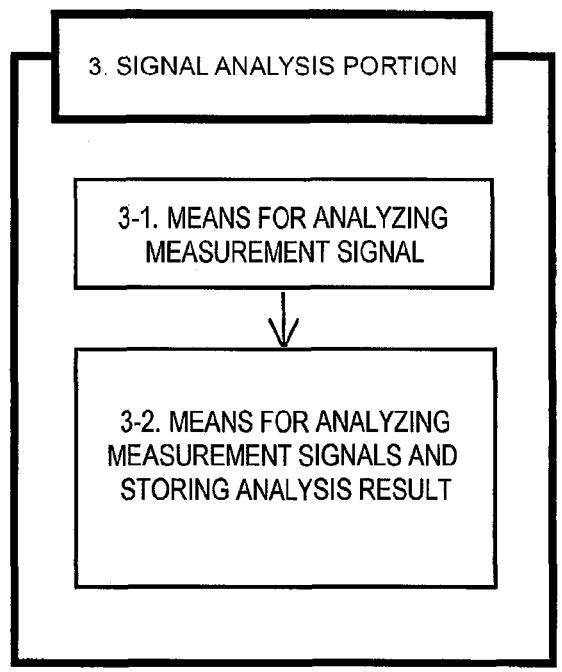
FIG. 8 is a view showing a flowchart in a signal analysis portion of the present example.

The signal analysis portion 3 in the stimulus presentation system includes subordinate means 3-1 and 3-2 shown in FIG. 8. In means for analyzing measurement signal 3-1, as shown in FIG. 9, regarding the analysis items of "information about cerebral activity signal", "gaze information", and "bio-signal information" and the restrictive conditions for analysis, any one item can be selected or input. Other items can be newly added to the respective items. Because the means for analyzing measurement signal 3-1 is the same as the means for analyzing reference reaction of user 1-2 in the user setting portion shown in FIG. 5, the description thereof will not be repeated. Herein, for the "information about cerebral activity signal", "delay time of cerebral activity" and "oxy-Hb signal" are selected. Furthermore, "1 to 10, 11 to 20" is selected for "designation of section"; "12" is selected for "designation of channel"; and "standardization" is selected. For the "gaze information", "variance in gazing time", "number of times of eye blinking", and "standardization" are selected. Moreover, as the restrictive condition for analysis, "20 seconds" is set for "gazing time". For the "bio-signal information", "heartbeat", "reaction time", and "standardization" are selected.

Means for analyzing measurement signal and storing analysis result 3-2 analyzes the measurement signal and stores the analysis result.

Figure 10:
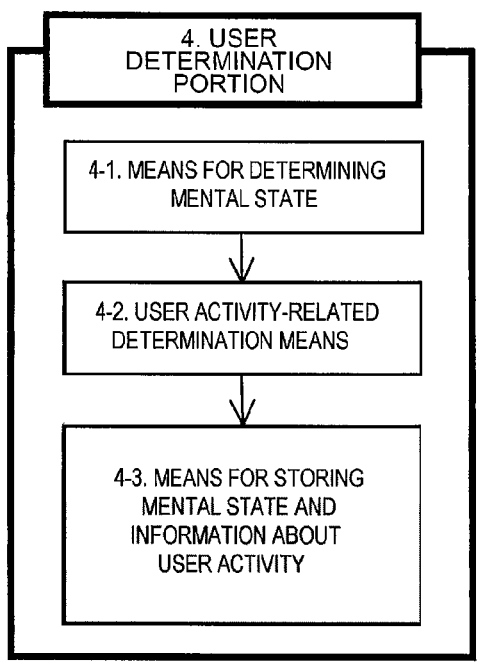
FIG. 10 is a view showing a flowchart in a user determination portion of the present example.

The user determination portion 4 in the stimulus presentation system includes subordinate means 4-1 to 4-3 shown in FIG. 10. In means for determining mental state 4-1, a mental state is determined by using the signal analyzed by the signal analysis portion 3.

Figure 11:
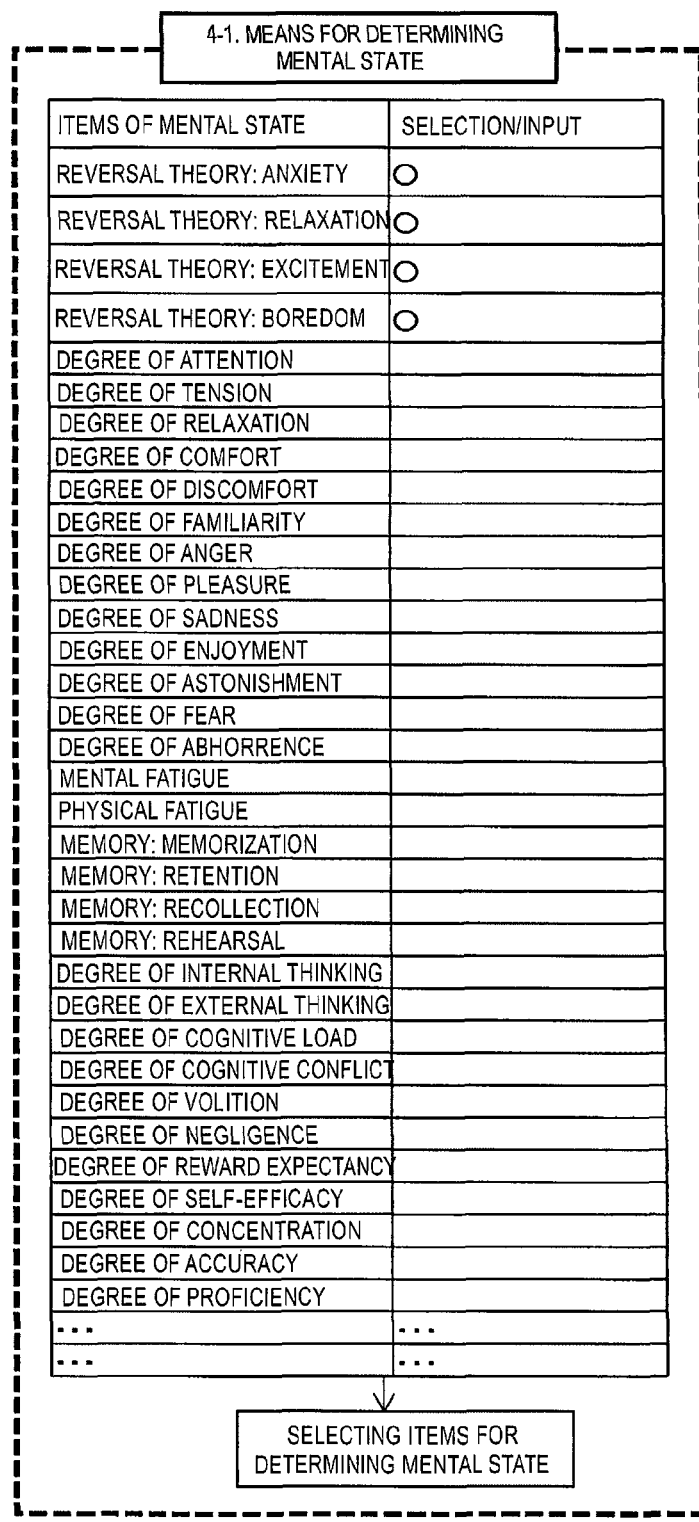
FIG. 11 is a view showing an example of how to set a user interface in the user determination portion of the present example.

As shown in FIG. 11, regarding the determined mental state of a user, from among "Reversal Theory: anxiety", "Reversal Theory: relaxation", "Reversal Theory: excitement", "Reversal Theory: boredom", "degree of attention", "degree of tension", "degree of relaxation", "degree of comfort", "degree of discomfort", degree of familiarity", "degree of anger", "degree of pleasure", "degree of sadness", "degree of enjoyment", "degree of astonishment", "degree of fear", "degree of abhorrence", "mental fatigue", "physical fatigue", "memory: memorization", "memory: retention", "memory: recollection", "memory: rehearsal", "degree of internal thinking", "degree of external thinking", "degree of cognitive load", "degree of cognitive conflict", "degree of volition", "degree of negligence", "degree of reward expectancy", "degree of self-efficacy", "degree of concentration", "degree of accuracy", and "degree of proficiency", any one item can be selected or input as a mental state item. Other items can be newly added to the mental state item. According to the procedure described so far, mental state determination items are selected, and a mental state is determined. Herein, "Reversal Theory: anxiety, relaxation, excitement, boredom" is selected.

FIG. 12 shows an example of how to determine a mental state by using the trend of mental state based on Reversal Theory and using the analysis signal. Herein, the Reversal Theory will be described. The theory is a motivation theory proposed by Apter (Reversal theory: Motivation, emotion and personality, Apter, Michael J. Florence, Ky., US: Taylor & Frances/Routledge. (1989). Viii 208 pp.), and is characterized in that four motivational states are dynamically reversed due to a certain motive. The motivational states form four pairs including telic (goal-oriented)-paratelic (activity-oriented), conforming-rebellious, mastery-sympathy, and focused on self-focused on others.

Herein, the motivational state (hereinafter, referred to as "mental state") of telic (goal-oriented)-paratelic (activity-oriented) relating to the user activity and the reversal thereof will be described. Regarding this pair, by the abscissa indicating the level of arousal (high-low) and the ordinate indicating hedonic tone, the mental state is classified into four types. The state in which a subject has a high level of arousal and is comfortable is defined as "excitement"; the state in which a subject has a high level of arousal and is uncomfortable is defined as "anxiety"; the state in which a subject has a low level of arousal and is comfortable is defined as "relaxation"; and the state in which a subject has a low level of arousal and is uncomfortable is defined as "boredom".

For example, in the case in which a user performs an activity by giving priority to the achievement of a goal (telic state), when the user has a high level of arousal and a high level of discomfort, it is considered that the user may be in a mental state of being anxious about the achievement of a goal. In contrast, when the user has a low level of arousal and a high level of comfort, it is considered that the user may be in a relaxed (stable, composed) mental state.

Furthermore, while undergoing transition to the telic mode (thick line) or to the paratelic mode (dotted line) shown in FIG. 12, sometimes the mental state is also reversed to the mental states of the upper and lower portions and the left and right sides (directions of bilateral arrows shown in FIG. 12) due to a certain motive. For example, even when a user performs an activity in a relaxed (stable, composed) mental state in the goal-oriented telic mode, if the user is inspired by a motive that accelerates cognitive transformation, the mental state is reversed to the paratelic mode (activity-oriented). In this case, when the user undergoes transition to the uncomfortable state from the comfortable state, the mental state becomes "boredom", and when the user undergoes transition to a high level of arousal from a low level of arousal, the mental state becomes "excitement".

However, in the related art, for example, only a degree of arousal is taken as a discrimination target by using brainwave or gaze information. Consequentially, even when it is possible to determine that the user is in the mental state of "arousal", whether the user is in the state of "excitement" or the state of "anxiety" cannot be determined. As a result, inappropriate support or activity assistance is likely to be provided for the user.

In the present example, regarding the "cerebral activity of the stimulus-related region", "cerebral activity of regions other than the stimulus-related region", "heartbeat", "eye blinking", and "variance in gazing time" shown in FIG. 13, the changes (increase, decrease, no change) in numerical values of the reference reaction of the user or the changes in numerical values at the resting time can be combined together, and the four mental states can be determined based on the Reversal Theory.

The "cerebral activity of the stimulus-related region" refers to the activity performed at the functional region of the brain that is most closely related to the user's activity. For example, in the case of the activity of memorizing letters, the activity results from the prefrontal region. The change in a level of cerebral activity of the stimulus-related region is also used for mental state determination. Furthermore, it is also important information for reading out whether the user activity set by using the present stimulus presentation system is being performed.

The items and the mode of change that are used for determining the respective mental states are as shown in the example of how to determine a mental state in FIG. 13. Herein, the mental state described in the section of the means for determining mental state can also be determined by combining the cerebral activity information, the gaze information, other bio-information, and behavioral information together. The determination results thereof are stored in means for storing mental state and information about user activity 4-3. In this way, the user can understand his/her own mental state while performing an activity.

Figure 14:
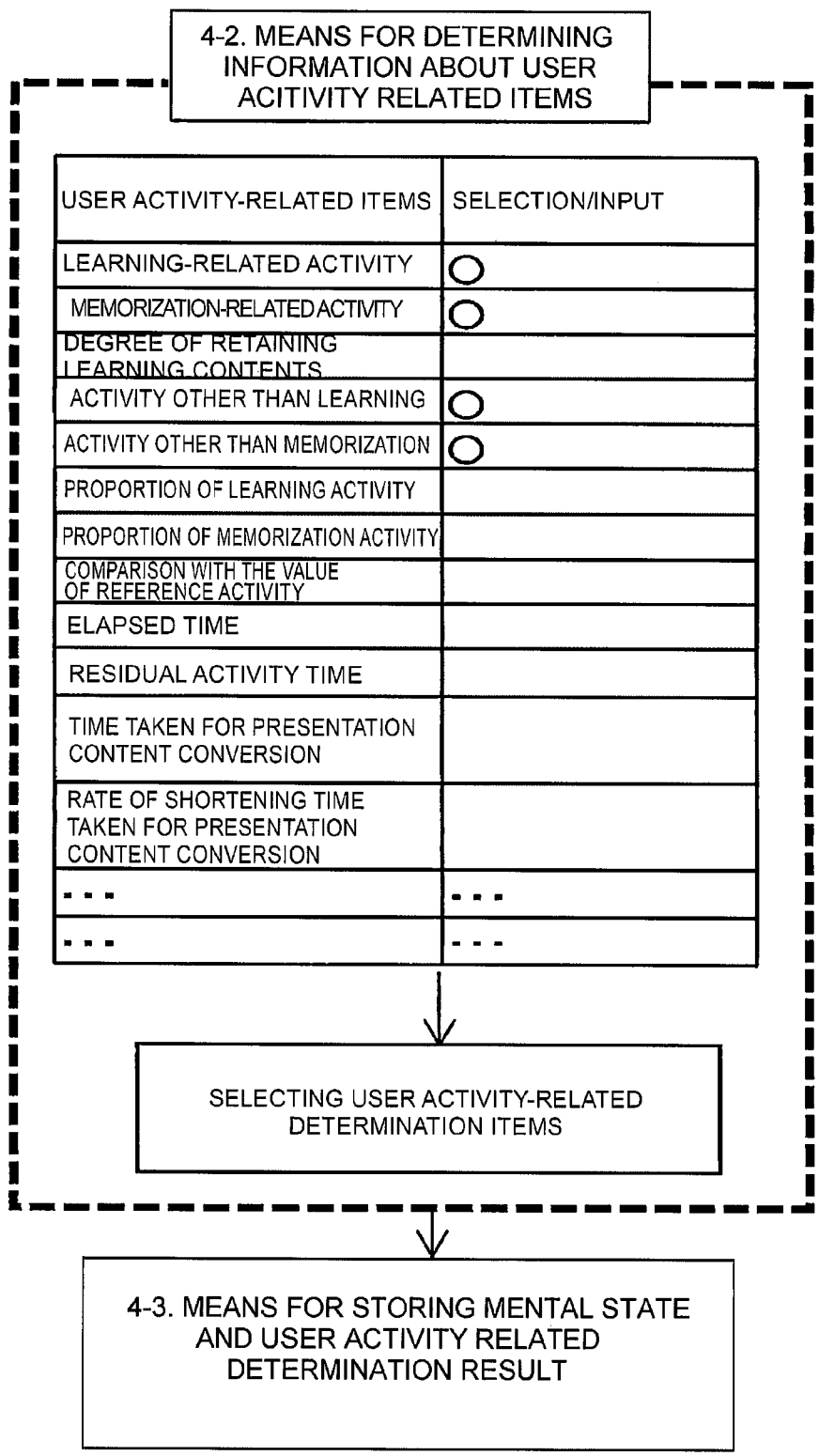
FIG. 14 is a view showing an example of how to set a user interface in the user determination portion of the present example.
Figure 15:
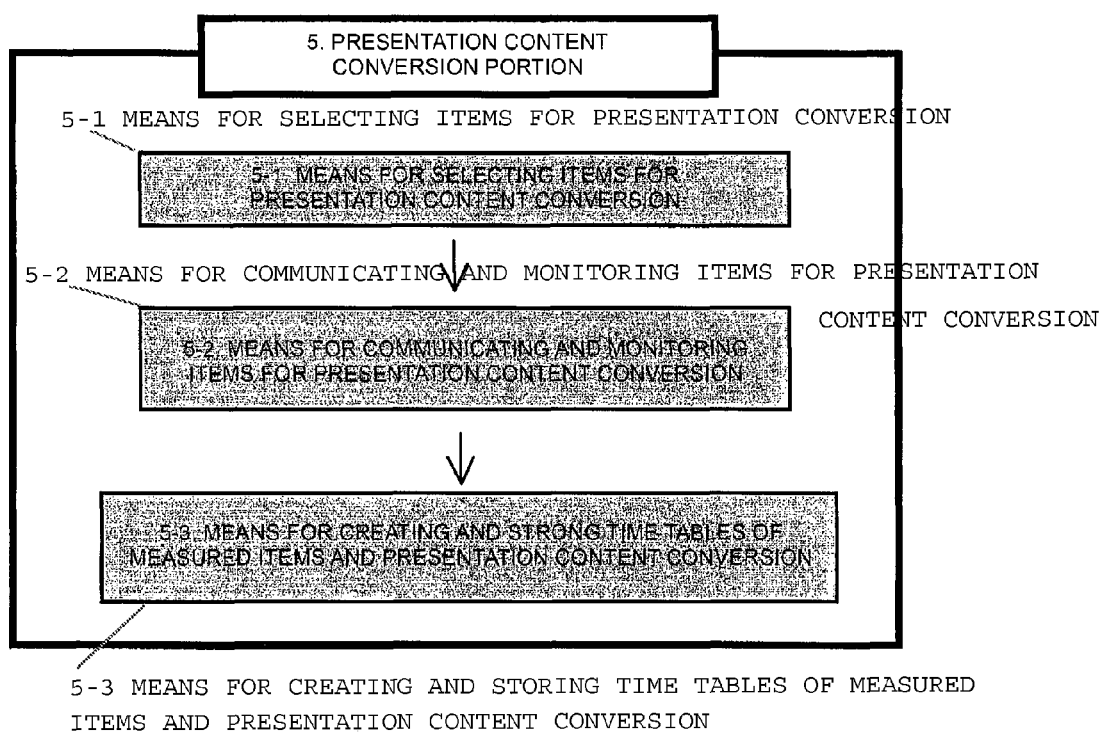
FIG. 15 is a view showing a flowchart in a presentation content conversion portion of the present example.

In user activity-related determination means 4-2, the information about user activity is determined by using the signal analyzed by the signal analysis portion 3. As shown in FIG. 14, from among "learning-related activity", "memorization-related activity", "degree of retaining learning contents", "activity other than learning", "activity other than memorization", "proportion of learning activity", "proportion of memorization activity", "comparison with level of reference activity", "elapsed time", "residual activity time", "time taken for presentation content conversion", and "rate of shortening time taken for presentation content conversion", any one item can be selected or input as a user activity-related item required to be determined. Other items can be newly added to the user activity-related item. According to the procedure described so far, the user activity-related item to be determined is selected. Herein, the "learning-related activity", "memorization-related activity", "activity other than learning", and "activity other than memorization" are selected. Determination results thereof are stored in the means for storing mental state and information about user activity 4-3. In this way, the user can understand to what extent he or she is performing the learning/memorization activity while performing the activity. The presentation content conversion portion 5 in the stimulus presentation system includes subordinate means 5-1 to 5-3 shown in FIG. 15. Means for selecting items for presentation content conversion 5-1 selects and stores the items for presentation content conversion, based on the analysis signal, mental state of the user, and activity state of the user.

Figure 16:
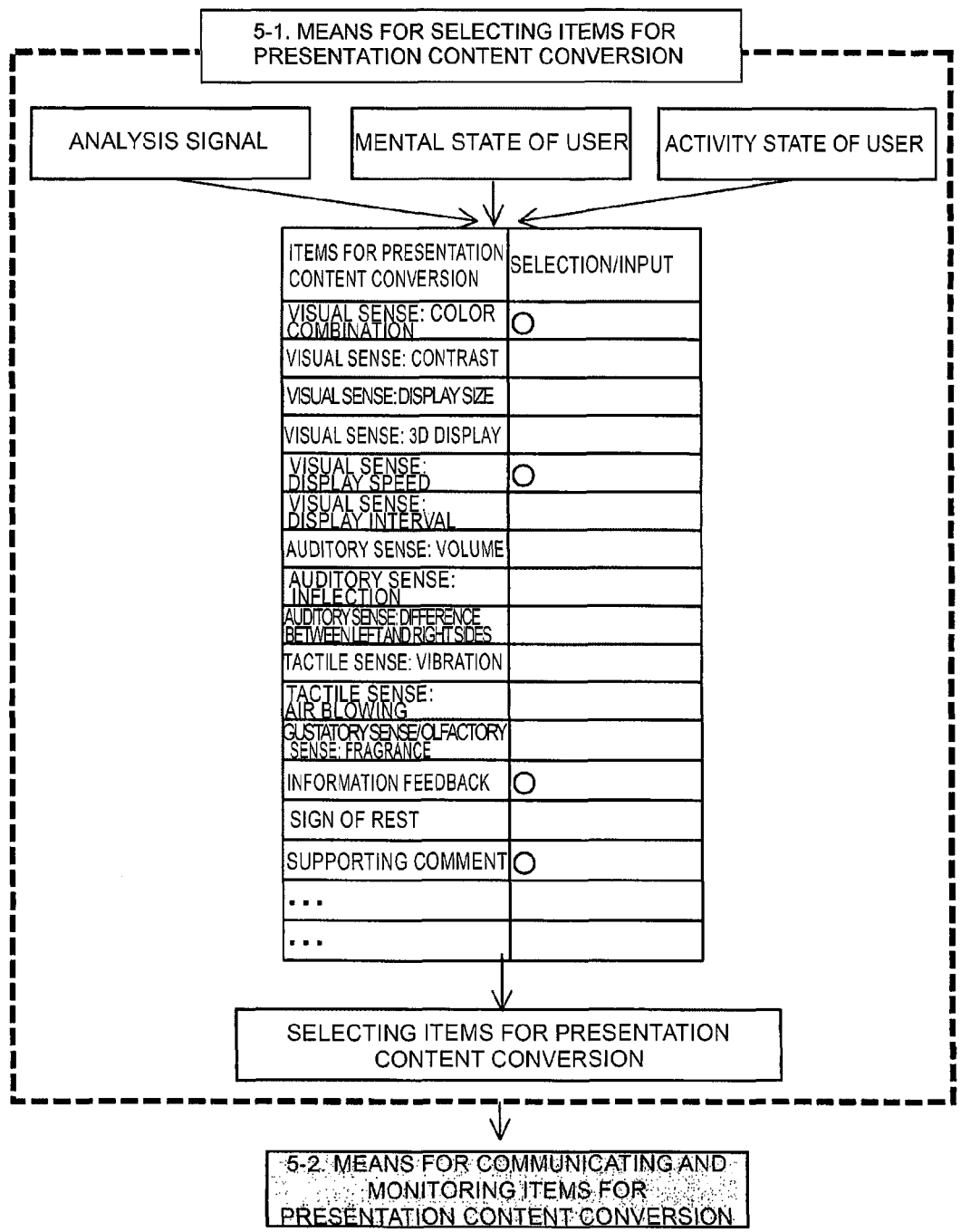
FIG. 16 is a view showing an example of how to set a user interface in the presentation content conversion portion of the present example.

As shown in FIG. 16, from among "visual sense: color combination", "visual sense: contrast", "visual sense: display size", "visual sense: 3D display", "visual sense: display speed", "visual sense: display interval", "auditory sense: volume", "auditory sense: inflection", "auditory sense: difference between left and right sides", "tactile sense: vibration", "tactile sense: air blowing", "gustatory sense/olfactory sense: fragrance", "information feedback", "resting sign", and "supporting comment", any one item can be selected or input as an item of presentation content required to be converted. Other items can be newly added to the item of presentation content to be converted. According to the procedure described so far, the items for presentation content conversion are selected/stored.

FIG. 17 shows an example of how to select items for presentation content conversion. Currently, based on the Reversal Theory, the mental state of a user has been determined to be "anxiety". Being in the state of anxiety, the user may not be able to continue the activity. That is, the anxious mental state is inappropriate as a mental state in which the user continues the activity, and accordingly, the user needs to be inspired by a motive for inducing/revering the mental state to the relaxed state that is optimal for the user activity.

An example of how to convert the presentation content so as to inspire the user by such a motive is shown in the lower part of FIG. 17. Herein, it is determined that the color combination of the presented problem is to be changed; the display speed of the presented problem is to be reduced 10%; feedback is to be provided for the information about the user activity; and a supporting comment is to be provided. A combination of these items is stored beforehand as a default pattern of the presentation content conversion, such that presentation content conversion can be performed for each of mental states in a predetermined way by the default pattern. Alternatively, the presentation content conversion corresponding to the level of mental state that changes from moment to moment can also be performed.

By means for communicating and monitoring items for presentation content conversion 5-2, the selected items for presentation content conversion are communicated by a monitor or a speaker, and the change in user activity is continuously monitored. When the user activity is continuously performed based on the presentation content converted by the presentation content conversion, the measurement data is sent to and processed in the user measurement portion, the signal analysis portion, and the user determination portion. In this way, when the user continuously performs an activity, it shows that the presentation content is making the user be in an appropriate mental state, and thus the user can perform the activity in an optimal mental state.

As shown in FIG. 18, the means for creating and storing measurement time table and information about presentation content conversion 5-3 can create and store data of a time table of the measurement items and a time table of presentation content conversion after the end of user activity, by using the analysis signal, the mental state of the user, the history of the user activity, and the history of the presentation content conversion.

Figure 19:
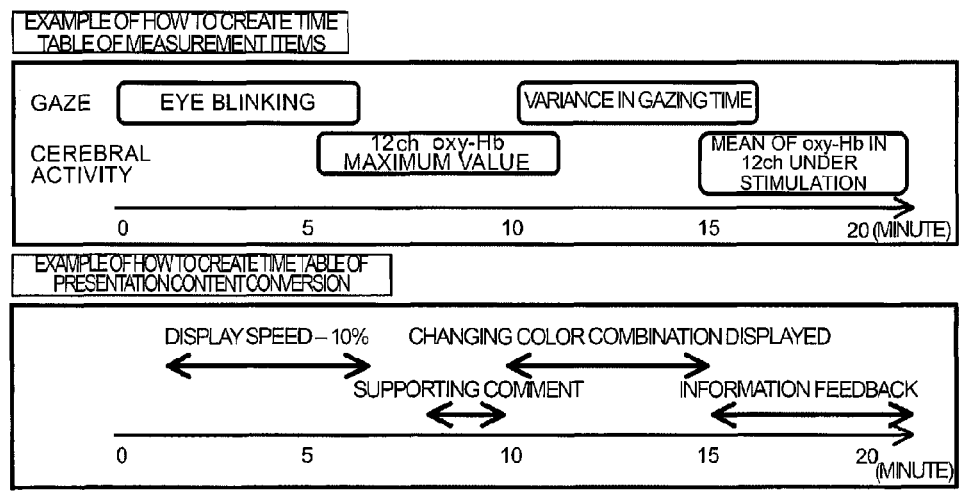
FIG. 19 is a view showing an example of how to create a timetable of measurement items and an example of how to create a timetable of presentation content conversion of the present example.

FIG. 19 shows an example of how to create a time table of the measurement items and how to create a time table of presentation content conversion. For example, regarding the time table of the measurement items, when the user performs an activity of memorizing letters for 20 minutes, it is not necessary to measure all items of the gaze information and the cerebral activity information. The time table shows that only the "eye blinking", "variance in gazing time", "maximum value of oxy-Hb of 12 ch", and "mean of oxy-Hb of 12 ch under stimulation" need to be measured at every predetermined clock time. If measurement is performed based on this information, the strain that the user wearing the measurement instrument feels can be reduced.

Regarding creation of the time table of presentation content conversion, for example, when the user performs an activity of memorizing letters for 20 minutes, the time table shows that only the "10% of reduction in display speed", "presentation of supporting comment", "changing color combination displayed", and "information feedback" need to be performed at every predetermined clock time. The time table of presentation content conversion performed at every clock time is the information that makes the user be in an optimal mental state. Consequentially, when the user performs the same or similar activities, if such a time table of presentation content conversion is used, the strain that the user wearing the measurement instrument feels can be reduced.

Figure 20:
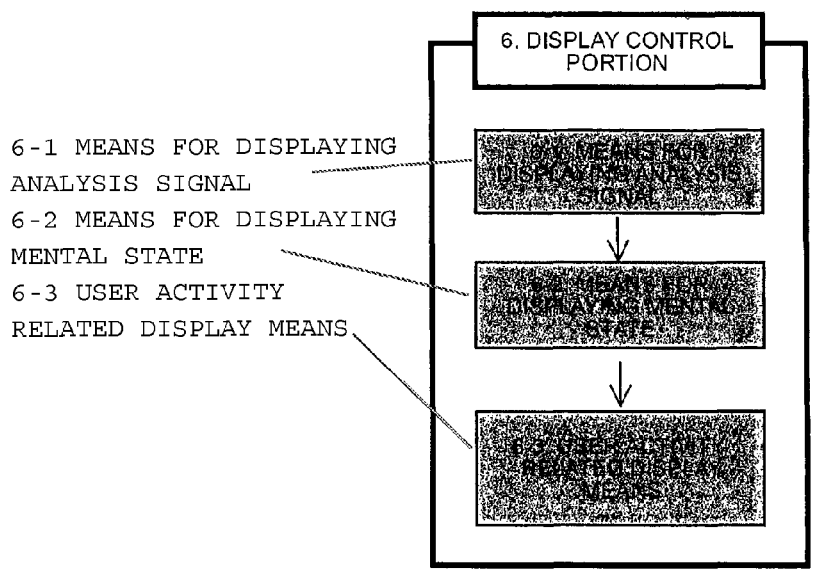
FIG. 20 is a view showing a flowchart in a display control portion of the present example.

The display control portion 6 in the stimulus presentation system includes subordinate means 6-1 to 6-3 shown in FIG. 20. Means for displaying analysis signal 6-1 displays the analysis result stored in the signal analysis portion 3. Means for displaying mental state 6-2 displays the mental state stored in the user determination portion 4. User activity-related display means 6-3 displays information about user activity stored in the user determination portion 4.

Figure 21A:
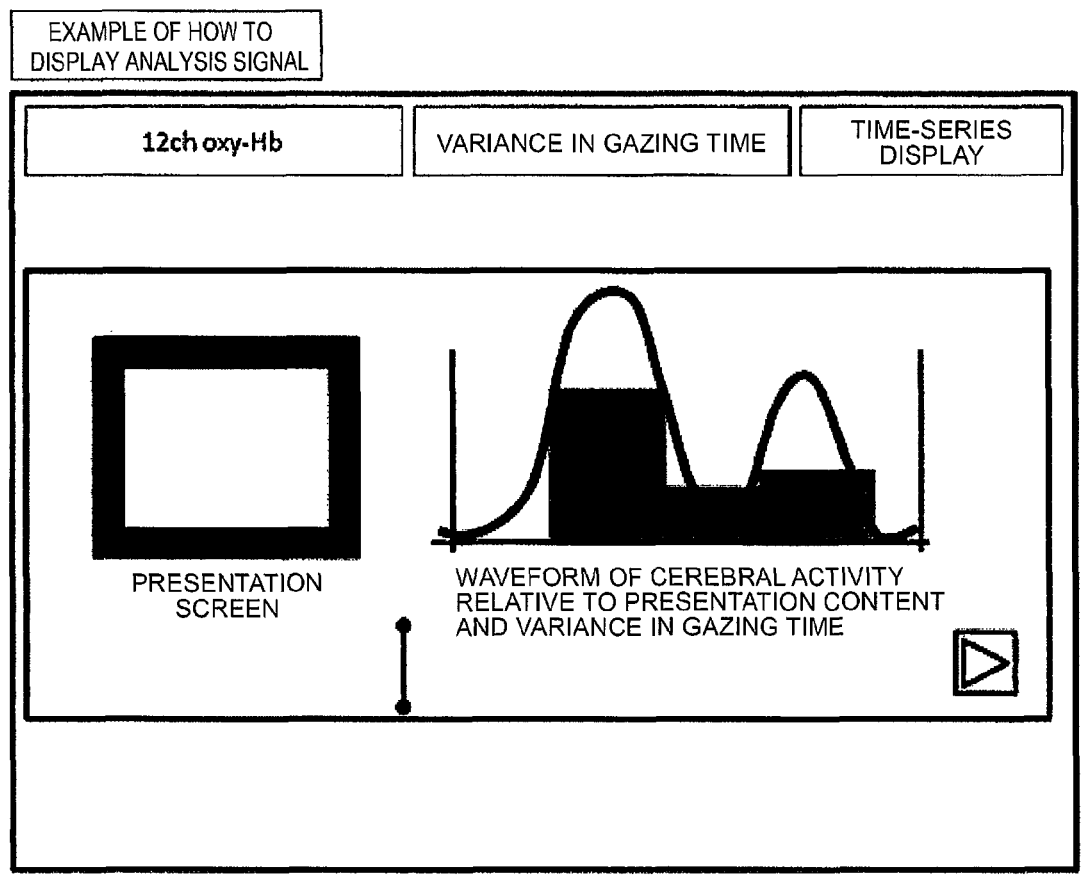
FIGS. 21A and 21B are views showing examples of how to display analysis signals in the present examples.
Figure 21B:
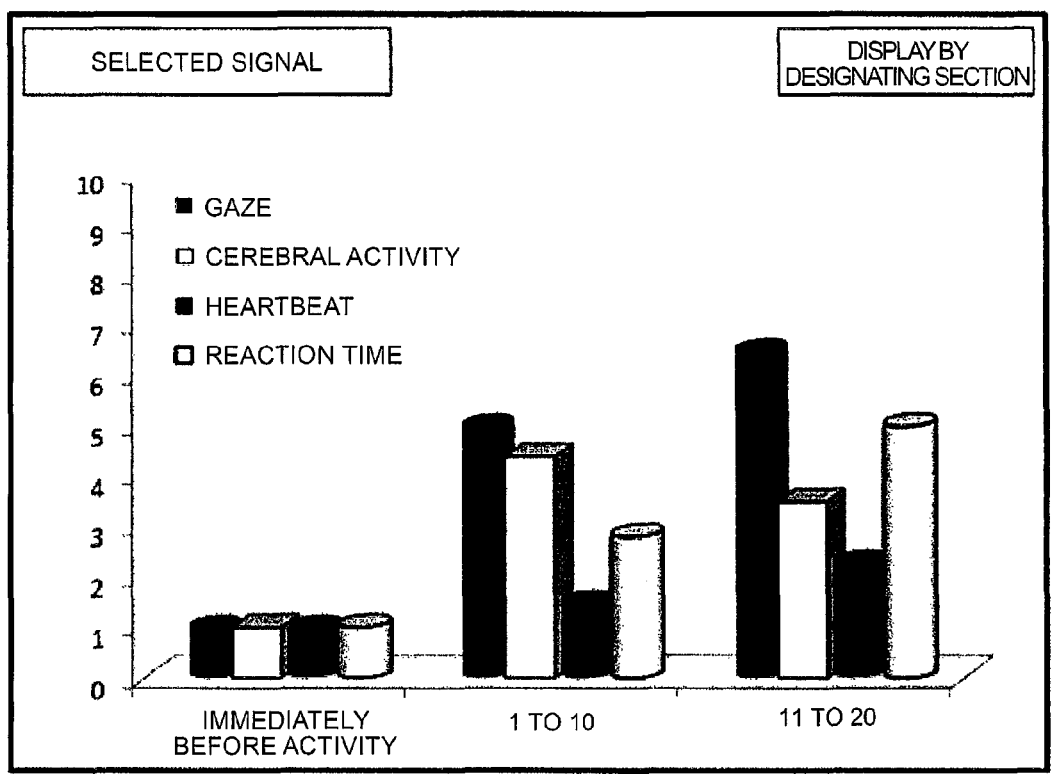

FIG. 21 shows two examples of how to display analysis results. FIG. 21A shows 12ch, oxy-Hb signal, the variance in gazing time, and the screen content presented to the user in a time-series manner. By dragging a slide bar in the lower portion, it is possible to simultaneously check the presentation content displayed on the screen at every clock time and the change in the waveform of cerebral activity and in the variance in gazing time corresponding to the presentation content. FIG. 21B shows how to display the selected signals ("gaze", "cerebral activity", "heartbeat", and "reaction time") by designating sections ("immediately before activity" and means of 1 minute to 10 minutes and 11 minutes to 20 minutes). The data may be standardized by regarding the numerical value obtained immediately before an activity as being 1. In this way, the change in trend of the activity section can be checked.

Figure 22A:
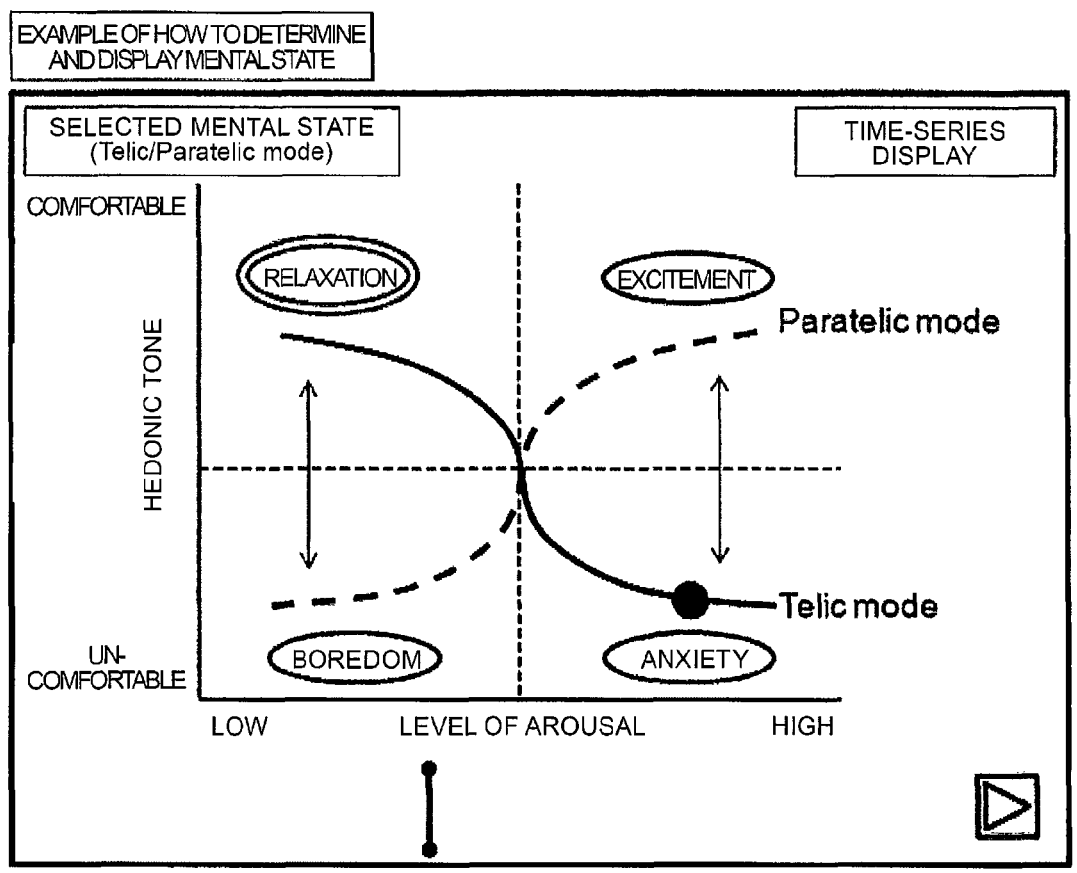
FIGS. 22A and 22B are views showing examples of how to determine and display mental states in the present examples.
Figure 22B:
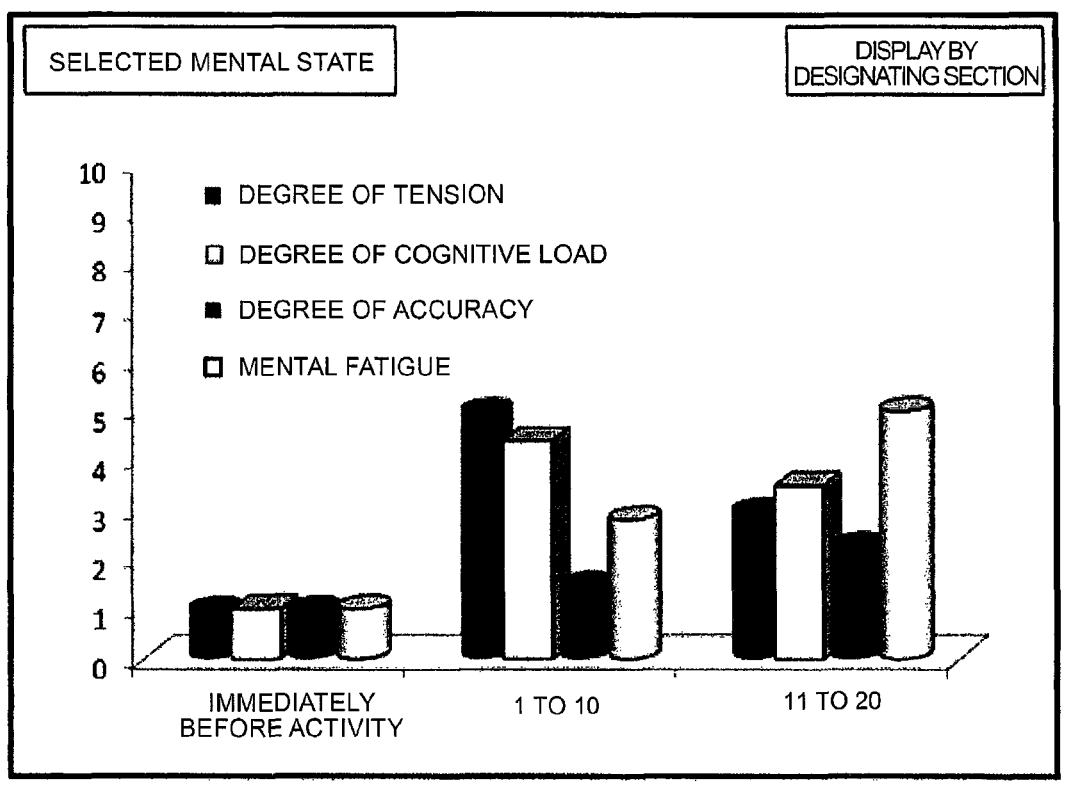

FIG. 22 shows two examples of how to determine and display mental states. FIG. 22A shows the position of the user state in the axes of Reversal Theory. By dragging a slide bar in the lower portion, it is possible to check the trend of mental state at every clock time. FIG. 22B shows how to display the selected mental states (herein, for example, "degree of tension", "degree of cognitive load", "degree of accuracy", and "degree of mental fatigue" are shown) by designating sections ("immediately before activity" and means of 1 minute to 10 minutes and 11 minutes to 20 minutes). The data may be standardized by regarding the numerical value obtained immediately before an activity as being 1. In this way, the change in trend of the activity section can be checked.

Figure 23A:
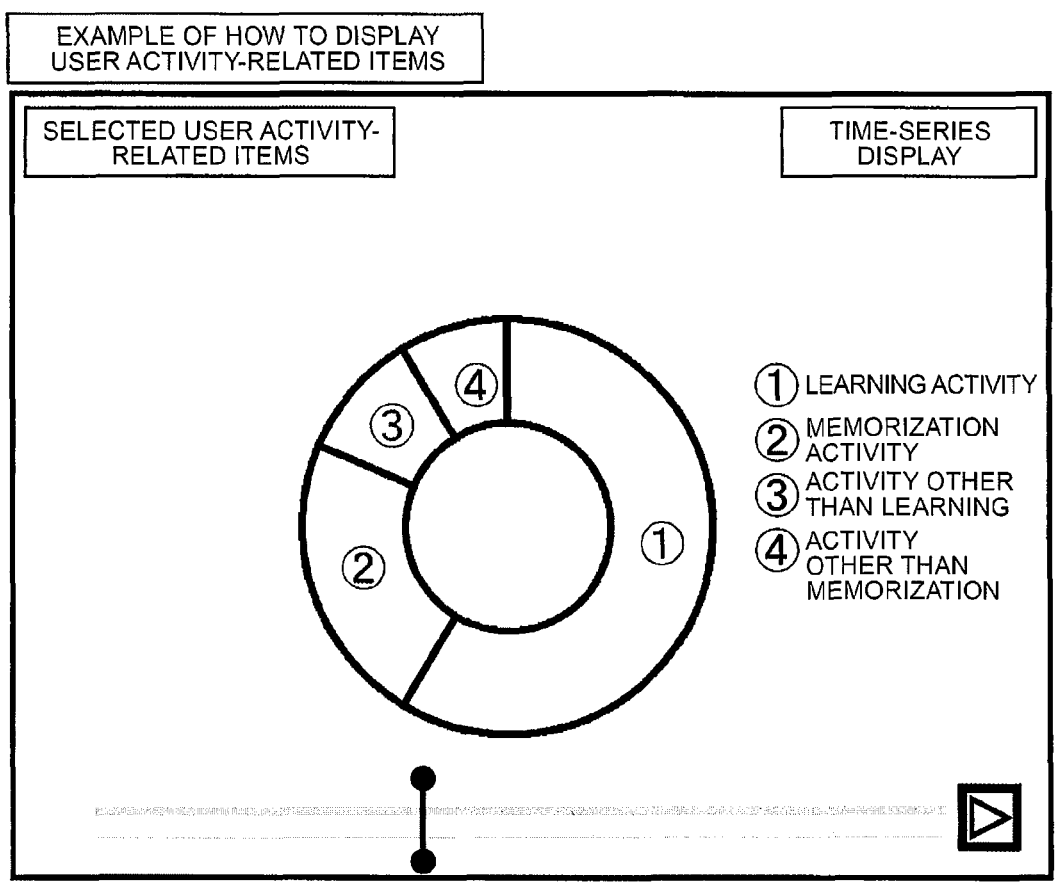
FIGS. 23A and 23B are views showing examples of how to display user activity-related items in the present examples.
Figure 23B:
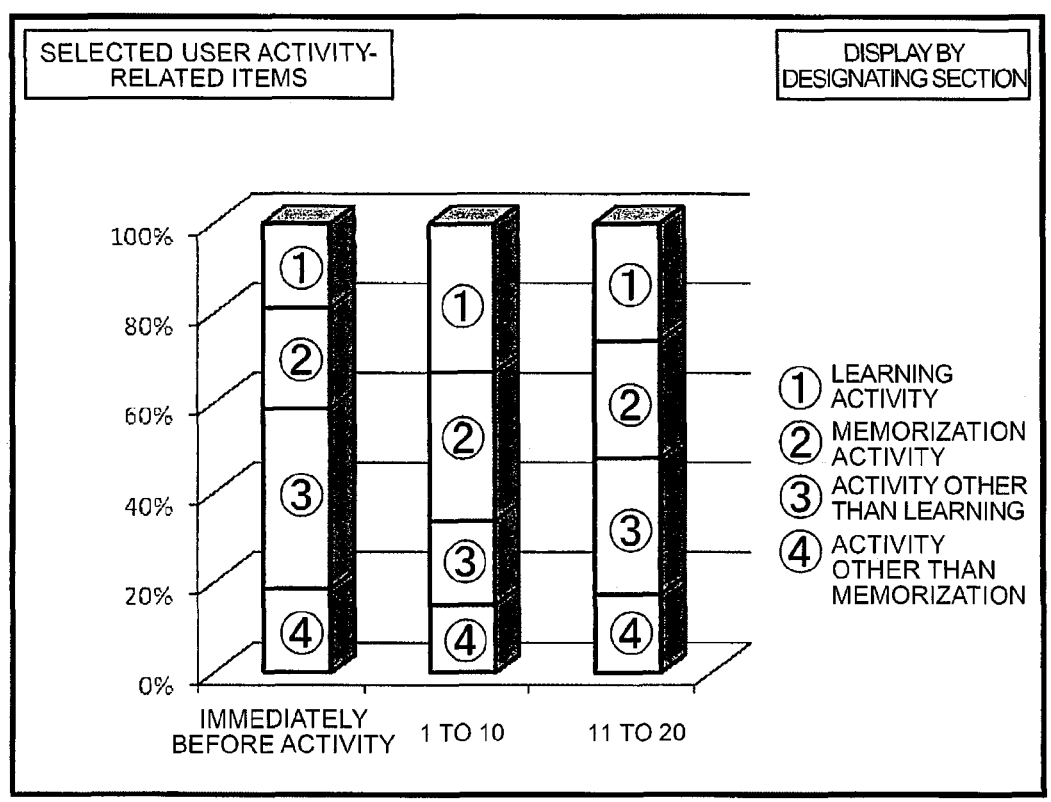

FIG. 23 shows two examples of how to display user activity-related items. Regarding "learning activity", "memorization activity", "activity other than learning", and "activity other than memorization", which are selected user activity-related items, FIG. 23A shows the change in relative proportion of these items at every clock time. By dragging a slide bar in the lower portion, it is possible to check the trend of user activity items at every clock time. FIG. 23B shows the selected user activity items by designating sections (proportion of value of each of "immediately before activity", "1 minute to 10 minutes", and "11 minutes to 20 minutes"). The data may be standardized by regarding the total of the numerical value obtained immediately before activity as being 100%. In this way, the change in proportion in trend of the activity section can be checked.

The storage portion 7 in the stimulus presentation system stores the information obtained in each portion of the stimulus presentation system. By using the information, analysis can be newly performed, and by accumulating data, a database can be created. As a result, the mental state of a user and the information about the user activity can be more accurately determined, and accuracy of the information about presentation content conversion can be further improved. Consequently, the activity of a user can be effectively supported.

(Other Application Examples)

The stimulus presentation system of the present invention is a stimulus presentation system which changes the presentation content of a problem based on the mental state determined by measuring gaze and cerebral function. Accordingly, if this system is applied to support learning of a user in an educational field, the user is made be in an optimal mental state and can efficiently continue learning.

Furthermore, providing time tables of presentation content conversion that are optimal as learning materials, the stimulus presentation system can provide materials effective for learning.

(Other Application Examples)

With the stimulus presentation system of the present invention, the mental state of a user can be determined. Accordingly, the system can be applied to the fields of user interface, advertisement, design, marketing, and the like.

(Other Application Examples)

The stimulus presentation system of the present invention can determine the mental state of a user. Accordingly, the system makes it possible to understand the mental state of a diseased patient who has difficulty in communication. Moreover, by changing the presentation contents based on the determined mental state, it is possible to change the mental state of the patient.

REFERENCE SIGNS LIST

11 . . . arithmetic device, 12 . . . user, 13 . . . cerebral activity information-measuring instrument, 14 . . . gaze information-measuring instrument, 15 . . . presentation monitor

The invention claimed is:

1. A stimulus presentation system comprising:
a monitor to display information to a user;
a first instrument to measure a gaze of the user including an amount of eye blinking and a variance in gazing time;
a second instrument to measure cerebral activity of the user including;
an arithmetic unit connected to the display, the first instrument, the second instrument, and which is configured to:
measure a reference state of the user based on a first measured gaze and a first cerebral activity of the user when a stimulus is displayed on the monitor to the user and when one or more measurement conditions are satisfied;
obtain a second measured gaze and a second measured cerebral activity of the user when a presentation content including a problem is displayed on the monitor to the user;
analyze the second measured gaze and the second measured cerebral activity;
determine a mental state of the user based on the analysis of the second measured gaze and the second measured cerebral activity;
cause one or more predetermined changes to the display of the presentation content on the monitor to the user based on the determined mental state; and
display the presentation content including the changes thereto, the second measured gaze, the second measured cerebral activity, and the determined mental state in a time-series manner,
wherein the first measured gaze includes a first amount of eye blinking and a first variance in gazing time,
wherein the second measured gaze includes a second amount of eye blinking and a second variance in gazing time, and
wherein the mental state is determined from results of the second measured gaze, the second measured cerebral activity and the reference state based on Reversal Theory.

2. The stimulus presentation system according to claim 1, wherein the arithmetic unit is further configured to:
correct a time lag between the first measured gaze and the first measured cerebral activity information from the point in time when the stimulus is presented to the user.

3. The stimulus presentation system according to claim 1, wherein the arithmetic unit is further configured to:
select measurement data of cerebral function relative to the stimulus based on data-effective conditions.

4. The stimulus presentation system according to claim 1, wherein the arithmetic unit is further configured to:
select items for changing the presentation contents of the problem based on the determined mental state.

5. The stimulus presentation system according to claim 1, wherein the arithmetic unit is further configured to:
create a time table of measurement items of the user based on the analysis of the second measured gaze and the second measured cerebral activity.

6. The stimulus presentation system according to claim 1, wherein the arithmetic unit is further configured to:
create a time table of presentation content conversion for the user based on the second measured gaze and the second measured cerebral activity.

7. The stimulus presentation system according to claim 1, wherein the arithmetic unit is further configured to:
display a slider bar for altering at least one of the second measured gaze, the second measured cerebral activity, the determined mental state, and the presentation content including the changes thereto.

8. The stimulus presentation system according to claim 1, wherein the arithmetic unit is further configured to:
display a trend of the determined mental state which has been determined based on Reversal Theory in a time-series manner.

* * * * *